(12) United States Patent
Goldin et al.

(10) Patent No.: US 11,738,148 B2
(45) Date of Patent: Aug. 29, 2023

(54) LOW PROFILE INTUITIVE PHARMACEUTICAL INJECTION DEVICE

(71) Applicant: Press-Q, Tel-Aviv (IL)

(72) Inventors: Ziv Goldin, Holon (IL); Amihay Avital, Petah Tikva (IL); Alexander Kurayev, Ramat Gan (IL)

(73) Assignee: Press-Q, Tel-Aviv (IL)

( * ) Notice: Subject to any disclaimer, the term of this patent is extended or adjusted under 35 U.S.C. 154(b) by 512 days.

(21) Appl. No.: 16/759,742

(22) PCT Filed: Oct. 29, 2018

(86) PCT No.: PCT/IL2018/051156
§ 371 (c)(1),
(2) Date: Apr. 28, 2020

(87) PCT Pub. No.: WO2019/087183
PCT Pub. Date: May 9, 2019

(65) Prior Publication Data
US 2021/0178073 A1   Jun. 17, 2021

Related U.S. Application Data

(60) Provisional application No. 62/578,545, filed on Oct. 30, 2017.

(51) Int. Cl.
*A61M 5/20* (2006.01)
*A61M 5/32* (2006.01)

(52) U.S. Cl.
CPC ........ *A61M 5/2033* (2013.01); *A61M 5/3202* (2013.01); *A61M 2005/202* (2013.01)

(58) Field of Classification Search
CPC .............. A61M 5/2033; A61M 5/3202; A61M 2005/202
See application file for complete search history.

(56) References Cited

U.S. PATENT DOCUMENTS

| | | | |
|---|---|---|---|
| 5,957,895 A | 9/1999 | Sage et al. | |
| 6,979,316 B1 | 12/2005 | Rubin et al. | |
| 2009/0124979 A1* | 5/2009 | Raymond | A61M 5/14244 604/195 |
| 2010/0049128 A1* | 2/2010 | McKenzie | A61M 5/14248 604/174 |
| 2016/0354553 A1* | 12/2016 | Anderson | A61M 5/19 |

(Continued)

*Primary Examiner* — Dung T Ulsh
(74) *Attorney, Agent, or Firm* — Bonini IP Law, LLC; Frank J. Bonini, Jr.

(57) ABSTRACT

Some embodiments of a low profile intramuscular auto-injector optionally comprise a contact surface contoured to fit a body surface. Optionally a height of the injector is less than ¼ a perimeter of the contact surface. Optionally a cover protects said contact surface. Optionally the device includes a priming mechanism coupled to the cover wherein removal of the cover activates the priming mechanism for priming the injector and/or increasing a height of the injector. Optionally the injector includes a cylindrical pharmaceutical reservoir rigidly attached to an injection needle. Optionally in a compact storage state the injection needle is at a low angle to the contact surface. Optionally during priming the needle and/or reservoir rotate to orient the needle at a higher angle to the contact surface.

19 Claims, 28 Drawing Sheets

(56) References Cited

U.S. PATENT DOCUMENTS

| | | | | |
|---|---|---|---|---|
| 2018/0133395 A1* | 5/2018 | Margairaz | ........... | A61M 5/3286 |
| 2018/0193557 A1* | 7/2018 | Johnson | ............ | A61M 5/14248 |
| 2019/0083709 A1* | 3/2019 | Cabiri | ................ | A61M 5/3134 |
| 2019/0160230 A1* | 5/2019 | Yudelevich | ......... | A61M 5/3232 |
| 2019/0175819 A1* | 6/2019 | Yang | ................... | A61M 5/1413 |
| 2019/0231973 A1* | 8/2019 | Cabiri | ................ | A61M 5/1454 |
| 2020/0016333 A1* | 1/2020 | Soares | ................. | A61M 5/158 |
| 2020/0222625 A1* | 7/2020 | Cabiri | ............... | A61M 5/14248 |

* cited by examiner

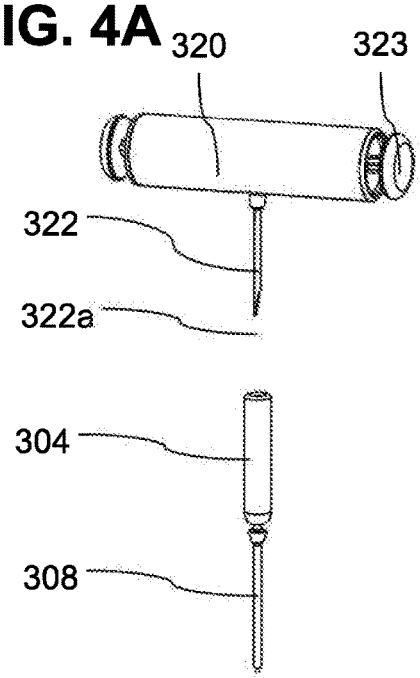
FIG. 4A
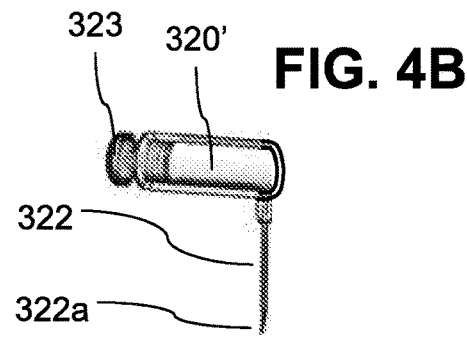
FIG. 4B
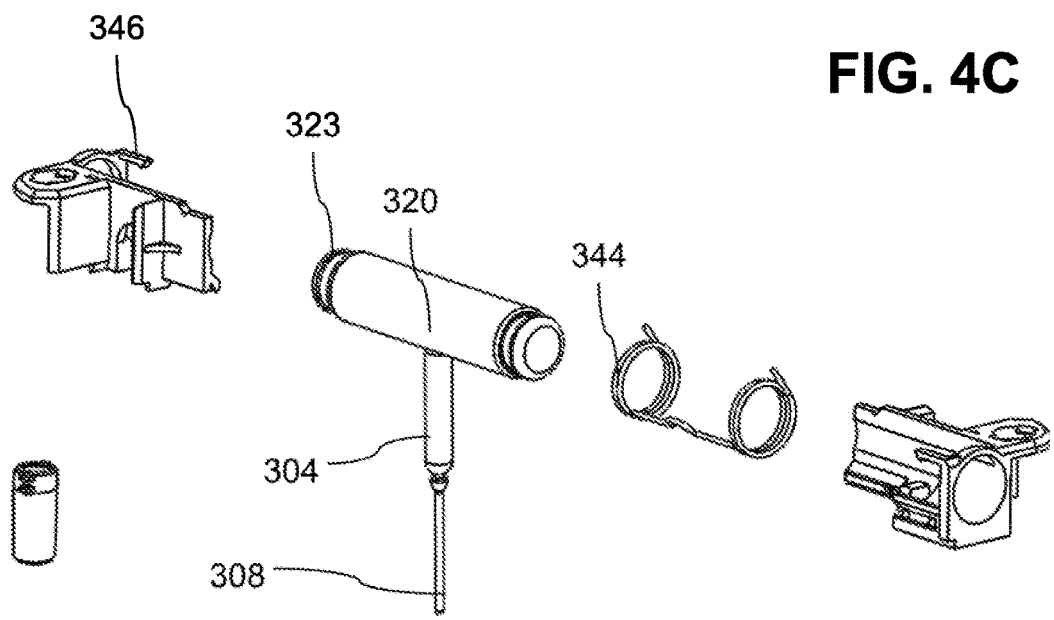
FIG. 4C
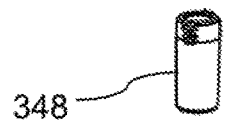

11,738,148 B2

LOW PROFILE INTUITIVE PHARMACEUTICAL INJECTION DEVICE

CROSS-REFERENCE TO RELATED APPLICATION/S

This application claims the benefit of priority under 35 USC § 119(e) of U.S. Provisional Patent Application No. 62/578,545 filed Oct. 30, 2017, the contents of which are incorporated herein by reference in their entirety.

FIELD OF THE INVENTION

Some embodiments of the invention relate to an automatic injection device for delivering a medicament to a patient. The injection device is especially but not only directed to usage under time pressure and/or in unsuitable surroundings and/or by unskilled persons. Optionally the device facilitates hand free operation during the medicament injecting for example avoiding mistakes by the operator during injection.

BACKGROUND OF THE INVENTION

U.S. Pat. No. 6,530,904 appears to disclose "A medical injector apparatus . . . for carrying medications, for example epinephrine."

U.S. Pat. No. 5,957,895 appears to disclose "a device for delivering a liquid therapeutic preparation into the body of a patient by injection into or through the skin of the patient." The device appears to comprise "a low-profile housing having a bottom surface adapted to be brought into contact with the skin of the patient. A reservoir is disposed within the housing for containing a liquid therapeutic preparation to be administered. An injection needle is disposed generally horizontally in the housing, and is adapted to communicate with the reservoir. The injection needle has a bent injection end which is adapted to project through a needle aperture in the bottom surface of the housing. A movable needle carrier is disposed in the housing for carrying the injection needle and for causing the injection end of the needle to project through the needle aperture upon movement of the needle carrier. The needle carrier and the injection needle are disposed in a side-by-side relationship with the reservoir in the housing in order to minimize the height of the housing above the bottom surface. As a result, the housing is sufficiently low in height to allow the device to be worn inconspicuously under the clothing of the patient."

U.S. Pat. No. 9,956,345 appears to disclose, "wearable automatic injection devices for administering a therapeutic agent to a patient's body at fast, controlled rates, for example, in a single fast bolus. Exemplary embodiments also provide methods for assembling wearable automatic injection devices for administering a therapeutic agent to a patient at fast, controlled rates. Exemplary embodiments also provide methods for using wearable automatic injection devices for administering a therapeutic agent to a patient at fast, controlled rates."

SUMMARY OF THE INVENTION

According to an aspect of some embodiments of the invention, there is provided an intramuscular auto-injector including: a contact surface on a proximal end thereof contoured to fit a body surface; a low-profile storage configuration wherein a height of the injector in the storage configuration is less than ¼ a perimeter of the contact surface; a cover protecting the contact surface; and a priming mechanism coupled to the cover wherein removal of the cover activates the priming mechanism, for priming the injector from the storage configuration to a primed configuration and wherein a height of the injector in the primed configuration is greater than the height of the injector in the storage configuration.

According to some embodiments the invention further includes an injection needle and wherein in the storage state an axis of the injection needle is oriented at an angle of less than 45 degrees with the contact surface and the priming mechanism is coupled to the injection needle for rotating the needle to an angle of greater than 45 degrees with the contact surface in the primed configuration.

According to some embodiments of the invention, the injection needle is rigidly attached to a pharmaceutical reservoir and wherein the rotating includes rotating the reservoir.

According to some embodiments of the invention, the rotating is around an axis of the reservoir.

According to some embodiments of the invention, the height of the injector in the storage configuration is less than twice a length of the injection needle.

According to some embodiments of the invention, the injector has cylindrical shape and the contact surface forms an end of the cylindrical shape.

According to some embodiments of the invention, the injector telescopes between the storage configuration and the primed configuration.

According to some embodiments the invention further includes an elastic energy storage device connected to the priming mechanism and wherein stored energy in the elastic energy storage device drives an increasing of the height of the injector between the storage configuration and the primed configuration.

According to some embodiments the invention further includes an elastic forcing member connected to the injection needle and wherein the elastic forcing member applies a force pushing a tip of the injection needle towards the contact surface in the primed configuration.

According to some embodiments of the invention the injector includes a cavity in which a pharmaceutical is stored and wherein is the stored configuration the cover is seals around the contact surface to prevent moisture from outside the injector from reaching the cavity.

According to some embodiments the invention further includes a needle sleeve sealing the needle from the cavity.

According to some embodiments of the invention the needle sleeve is attached to the cover.

According to an aspect of some embodiments of the invention, there is provided a method of intermuscular injection of a drug including: providing an injection device in a storage configuration having a contact surface on a distal end thereof and a cover covering the contact surface and wherein a height of the injector away from the contact surface in the storage configuration is less than a quarter a perimeter of the contact surface; removing the cover from the contact surface; priming the injection in response to the removing and wherein the priming includes increasing the height; placing the contact surface on a surface of a subject; pushing a proximal end of the injector towards the contact surface; and extending a point of an injection needle out a hold in the contact surface into the subject in response to the pushing.

According to some embodiments the invention further includes rotating an injection needle from an angle of less than 45 degrees to the contact surface in the storage configuration to an angle of greater than 45 degrees to the contact surface in a primed configuration.

According to some embodiments of the invention the injection needle is rigidly attached to a drug reservoir, wherein the rotating further includes rotating the drug reservoir.

According to some embodiments of the invention the rotating is around an axis of the drug reservoir.

According to some embodiments of the invention the injector has a cylindrical shape and wherein the contact surface forms and end of the cylinder and wherein the increasing the height include telescopic lengthening of the cylinder.

According to an aspect of some embodiments of the invention, there is provided a pharmaceutical cartridge including: a cylindrical reservoir having a longitudinal axis; and an injection needle rigidly connected to a wall of the reservoir and protruding from the wall at an angle of greater than 30 degrees to the longitudinal axis.

According to some embodiments the invention further includes a needle sleeve protecting a sterility of the injection needle.

According to some embodiments of the invention the reservoir is open on two ends thereof.

According to an aspect of some embodiments of the invention, there is provided a method of assembling an autoinjector including: supplying a cartridge with a cylindrical reservoir and needle protected by a sterile needle cover; filling the reservoir with a pharmaceutical in an aseptic environment; Inserting the cartridge filled with the pharmaceutical into a housing of the autoinjector; and collapsing the autoinjector to a compact state and wherein the compacting includes rotating the cartridge to orient the needle at a low angle to a contact surface of the injector. 22. The method of example 21, wherein the collapsing is in a direction substantially perpendicular to the contact surface.

According to some embodiments of the invention the rotating is around a longitudinal axis of the reservoir.

According to some embodiments of the invention the needle is rigidly attached to the reservoir.

According to some embodiments of the invention the needle extends perpendicular to the axis of the reservoir.

According to some embodiments the invention further includes attaching an outer cover to the autoinjector thereby holding the autoinjector is the compact state.

According to some embodiments of the invention the outer cover covers the contact surface.

According to some embodiments the invention further includes attaching the needle cover to the outer cover.

According to some embodiments of the invention the injector includes a cavity in which a pharmaceutical is stored and further including: sealing the cover to the cover to the autoinjector thereby preventing moisture from outside the injector from reaching the cavity.

In some embodiments, an auto-injection device for automatically injecting the contents of a reservoir 120 to a desired penetration depth includes an upper housing 101 and a lower housing 102 which interconnect movingly to each other creating a casing inside of which an injection module is positioned. The injection module optionally comprises at least one reservoir 120 that optionally contains a certain amount of fluid, an injecting means 122 which is optionally connected into the reservoir 120 for example, for pushing the fluid from the reservoir 120 into injecting means 122, and/or an elastic means 151 holding the upper housing 101 and the lower housing 102 at a first position relative to each other. Optionally when a force is applied on the upper housing 101 in the direction of the lower housing 102 the lower housing 102 and/or the upper housing 101 move to a second predefined position relative to each other. Optionally, the upper housing 101 pushes the reservoir 120 and/or with it the injecting means 122 into a position suitable for injecting the fluid. Optionally in the second position, applying of force upon the upper housing 101 inhibits a mechanism for pushing the fluid into the injecting means 122. Optionally, when the pressure on the housing is released the fluid is discharged through an injection needle.

In an advantageous embodiment, the elastic means 151 pushes the upper housing 101 away from the lower housing 102 into the direction of the first position thus activating the mechanism for pushing the fluid into the injection means 122

In an advantageous embodiment, achieving the $2^{nd}$ position is enough for activating the mechanism for pushing the fluid into the injection means 122.

In an advantageous further embodiment, the mechanism for pushing the fluid includes at least one reservoir 120 and at least one plunger 123 which is movable positioned inside the reservoir 120. Optionally. the fluid can be pushed into the injecting means 122 by moving the plunger 123 to push the fluid against the reservoir 120 and/or by moving the reservoir against the plunger 123 thus creating pressure and pushing the fluid into the injection means 122. This may be applied by circular or linear movement.

In an advantageous further embodiment, the reservoir 120 has a cylindrical shape and/or a circular cross section.

In an advantageous further embodiment, the upper housing 101 comprises a reservoir centering pin 111 which pushes the reservoir 120 and/or the injecting means 122. Optionally injection occurs while an operator holds the reservoir 120

In an advantageous further embodiment, the reservoir can be any reservoir comprised of a plunger and/or a reservoir having a round or cylindrical shape activated by rotation of the elastic means 121.

In an advantageous further embodiment through the pushing of the reservoir 120 and/or the medical needle 122, a part of the medical needle 122 is pushed outside of the casing and into the injection site on which the auto-injection device is positioned.

In an advantageous further embodiment, the upper housing 101 includes at least one rotation preventing pin 112, the plunger 123 optionally includes at least one rotation preventing socket 124 and/or the rotation preventing pin 112 sinks into rotation preventing socket 124 of the plunger 123 preventing rotational movement of the plunger 123 and/or of the reservoir 120. Optionally the reservoir 120 has at least one rotation preventing socket 124 whereas the rotation preventing pin 112 sinks in the rotation preventing socket 124 thus preventing rotational movement of the reservoir 120.

In an advantageous further embodiment, the auto-injection device comprises a propulsion means 121 which is connected to either the plunger 123 or to the reservoir 120 in such a way that it can use rotational energy either on the plunger 123 or on the reservoir 120 to create the movement that will push the internal wall against the plunger 123 or the plunger 123 against the internal wall thus applying pressure to the fluid and pushing it into the injection means 122, In an advantageous further embodiment, the propulsion means 121 includes a circular spring and/or a motor and/or a shape memory material In an advantageous further embodiment when an operator stops applying the force to be the upper housing and/or the elastic means 151 pushes the upper housing 101 away from the reservoir 120, the preventing pin 112 slides out of the rotation preventing socket 124. Optionally this facilitates activation of a propulsion means 121 to move the plunger 123 and/or the reservoir pushing the fluid into the injection means 122 and eventually into the subject.

In an advantageous further embodiment, the reservoir 120 is held to the bottom case 102 by the elastic means and/or by glue and/or a mechanical means, for example attached to the inner side of the bottom case 102 and/or the friction of the medical needle 122 with the penetrated body.

In an advantageous further embodiment, the auto-injection device includes a protective cover 103 which the operator may pull off the auto-injection device shortly before usage.

In an advantageous further embodiment, removing cover 103 primes the device for use.

In an advantageous further embodiment, a safety pin 131 is positioned to fixate the injection module so that it does not move from its position by mistake when a force is falsely applied to the auto-injection device. Optionally the pin is detached by the operator to prime the device before use.

In an advantageous further embodiment, the protective cover 103 includes at least one safety pin 131 which is positioned to fixate the injection module.

In an advantageous further embodiment, a time and/or content indicator 190 may be positioned between bottom case 102 and protective cover 103.

In an advantageous further embodiment, a time and/or content indicator 190 includes a body with one or more double sided glue, one and/or more hold/release feature on the side facing bottom case 102, printed or molded information of drug content, and/or a means of indicating time of use.

In an advantageous further embodiment, an adhesive substance is placed between the protective cover 103 and the lower housing 102. Optionally the adhesive is exposed when the protective cover is pulled off and can be used to attach the auto-injection device securely to a surface.

In an advantageous further embodiment, the medical needle 122 is held by a threshold mechanics that only allow it to exit the auto-injection device when a certain minimal force is applied on the upper part 101

In an advantageous further embodiment, the threshold mechanics include placing the injecting end of the medical needle 122 in such a way that it needs to penetrate a material that would not allow it to be pushed out of the auto-injection device when force under a certain level or threshold is applied.

In an advantageous further embodiment, the minimum force to overcome the threshold mechanics is equivalent of 500 gr.

In an advantageous further embodiment, the threshold mechanics comprises a septum and/or membrane material and/or a puncture seal membrane.

In an advantageous further embodiment, the threshold mechanics keeps the medical needle 122 sterile even after the seal 103 has been opened and/or acts as a second security line.

In an advantageous further embodiment, the threshold mechanics comprise a collapsing or breakable material in the mechanism that lowers the medical needle 122.

In an advantageous further embodiment, the desired penetration depth is reached as soon as the needle has reached muscle tissue.

In an advantageous further embodiment, the auto-injection device comprises indicating means 171 which indicate to the operator that the medical needle 122 has been pushed out of the auto-injection device to the fully intended length.

In an advantageous further embodiment, the auto-injection device comprises indicating means which is activated when the auto-injection device is primed and/or activated and/or indicate the time and/or or date of activation.

In an advantageous further embodiment, the auto-injection device comprises an indicating means which activates when the auto-injection device starts and/or finishes pushing the fluid into the needle In some embodiments, the indicating means may include a visual sign and/or a sound and and/or a haptic sign.

In an advantageous further embodiment, the auto-injection device comprises insulation around the reservoir 120 protecting the fluid inside from temperature fluctuations and/or from too high or too low temperatures.

In an advantageous further embodiment, the auto-injection device comprises a mechanism that pulls the mechanical needle 122 out of the surface after discharge of a dose of the drug.

In an advantageous further embodiment, the auto-injection device comprises a mechanism that protects the needle when the auto-injection device is detached from the injection surface for example by pushing a protective cylinder over the needle.

In an advantageous further embodiment, the auto-injection device comprises a mechanism that bends the medical needle after injection and/or after removal of the device from the injection site.

In an advantageous further embodiment, the auto-injection device comprises a mechanism that move the needle out of alignment after injection and/or after removal of the device from the injection site.

In an advantageous further embodiment, the needle 122 is positioned in the body of the plunger 123 in such a way that it is positioned in the center of the injection module and by that also in the center of the auto-injection device In an advantageous further embodiment, the propulsion means 121 includes a rotational spring.

In an advantageous further embodiment, the elastic means 151 includes a spring.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 4A and 4B are schematic views of a pharmaceutical reservoir in accordance with embodiments of the present invention;

FIG. 4C is a schematic exploded view of a cartridge assembly in accordance with an embodiment of the current invention;

PARTS LIST

Figure 1:
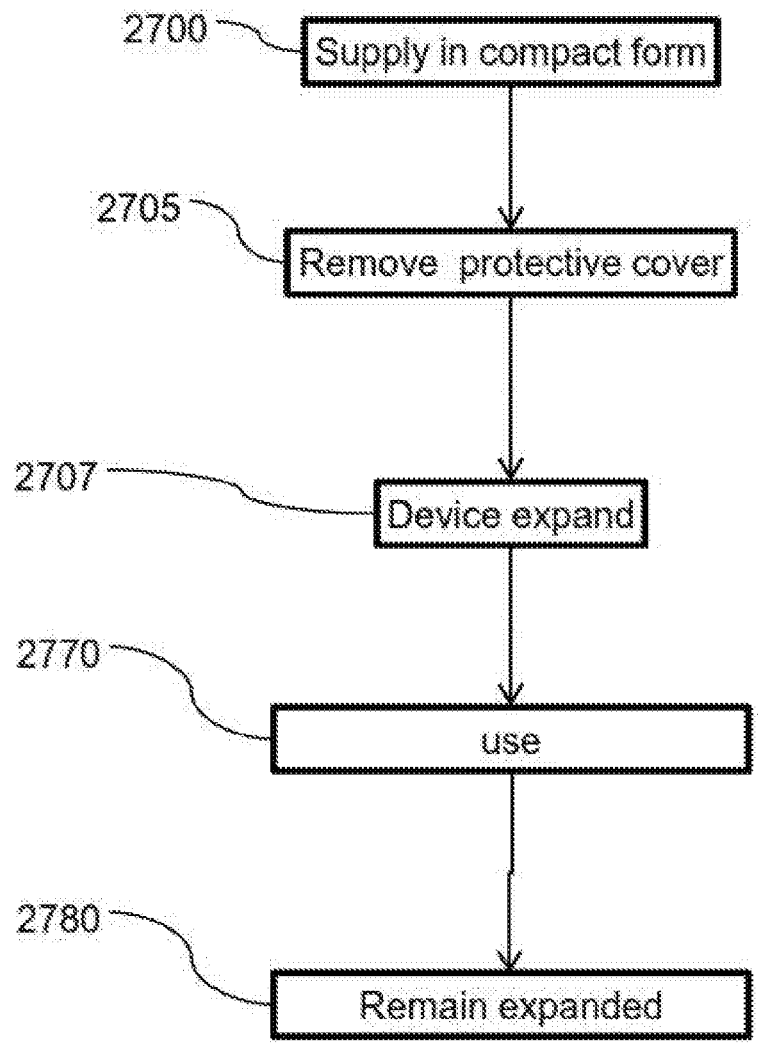
FIG. 1 is a flowchart illustration of a method of administering a pharmaceutical in accordance with an embodiment of the present invention.

100 Auto-injection device.
101 Upper housing.
102 Lower housing.
103 Protective cover.
111 reservoir centering pin.
112 rotation preventing pin.
113 driving pin.
114 driving slot.
120 Drug reservoir.
121 rotational spring—propulsion means.
122 medical needle.
122a needle tip.
123 Plunger.
124 rotation preventing socket.
125 rotational spring slot—internal wall.
126 air inlet.
127 manifold.
128 needle exit point.
131 safety pin.
132 hole.

150 Injection Module.
151 elevating spring—elastic means.
161 Adhesive Layer.
170 Activation display mechanism.
171 Time Display mechanism.
175 Detachable time and content indicator release pin.
180 Safety mechanism.
190 Detachable time and content indicator.
200 Drug indicator.
201 Complete action indicator—option A.
202 Complete action indicator—option B.
210 Planetary system.
211 Pluner pivot.

DETAILED DESCRIPTION OF A PREFERRED EMBODIMENT OF THE INVENTION

Overview

An aspect of some embodiments of the current invention relates to an autoinjector that having a shape that makes it easy to carry and/or to use in an emergency. For example, the device may intuitively facilitate proper use. For example, the injector may be shaped like an emergency button, may discourage pulling off immediately after needle insertion and/or may have a flat shape.

In some embodiments, the injector may be shaped like an emergency button. For example, the injector may have a substantially cylindrical shape (optionally a right cylinder with a cross section that may be round, square or rectangular alternatively or additionally the cylinder may be not be a right cylinder and/or may have another cross section). Optionally the device will have a substantially flat bottom with a contact surface for an injection site. Optionally the device is activated by pushing a dome shaped upper surface towards the contact surface. Optionally, the colors and/or shape of the device is selected to make it intuitive where the operator contacts the device and/or where the device contacts an injection zone. For example, the top pushing surface may have a domed shape and/or a dome overhanging a post and/or may be colored to catch the eyes of an operator. The bottom and/or contact surface is optionally not button shaped, for example it may be flat and/or not round and/or concave. Optionally a removable cap covers the contact surface. For example, the device may be primed by removing the cap.

In some embodiments, the device is configured to be activated by pushing an upper surface with a flat hand without grasping the device. For example. the upper surface may be relatively large and flat, discouraging grasping and/or may sink into a hole and/or may have an overhang that approaches a flat surface. Optionally, the hand position for activating the device differs from the hand position for removing the device.

An aspect of some embodiments of the current invention relates to an intermuscular auto-injector that has a flat storage configuration. in injection device expands telescopically when it is primed and/or is activated by pushing towards a contact surface and/or to contract a telescoping mechanism and/or to push a button towards the contact surface.

An aspect of some embodiments of the current invention relates to a cartridge for and autoinjector. For example, the cartridge may have a cylindrical reservoir directly and/or rigidly connected to an injection needle and/or a needle mount. Optionally, the needle and/or needle mount protrudes from a side wall of a cylindrical cartridge and/or is positioned in a central portion of the cartridge (e.g. in the more than ¼ of the length of the cartridge from either end of the cartridge and/or more than ⅛ the length and/or more than 1/10 the length). Optionally the needle is directed at an angle of between 0 to 10 degrees and/or between 10 to 30 degrees and/or between 30 to 60 degrees to the axis of the reservoir and/or at an axis of between 60 to 90 degrees and/or between 80 to 90 degrees. In some embodiments the reservoir has an opening on at least one end and/or can be filled with a standard and/or minimally modified filling machine. Optionally, the cartridge and/or the needle is configured be filled and/or sealed for sterility before insertion into the injector. For example, the cartridge may be filled with a needle covered by a needle sleeve. For example, the device may be filled by putting a pharmaceutical through an open end of the cylindrical reservoir into the reservoir and then inserting a cap into the open end. Optionally there may be a flange around the open end. In some embodiments, the reservoir may include more than one plunger. For example, a cylindrical reservoir may include an opening and a plunger at either end thereof.

An aspect of some embodiments of the invention relates to an auto injector with a rotating needle and/or cartridge. For example, the cartridge may rotate around the axis of a cylindrical reservoir thereof. Optionally, rotating the cartridge may increase an angle between the needle and a contact surface of the injector before needle insertion. Optionally, the rotation occurs while the needle remains protected and/or inside the housing of the injector. For example, the rotation may be over an angle of between 60 to 90 degrees and/or between 45 to 60 degrees and/or between 15 to 45 degrees.

In some embodiments, a medical injector is configured for use by an operator with little or no training in administrating the injection. Optionally the injector is configured to inhibit improper use. For example, the device may be developed for fool proof and/or intuitive use. For example, an operator may be under time pressure for example in case of emergency and/or in stressful surroundings, like a battle field and/or in working environments such as the outer space. In some embodiments, the device may facilitate fast and repetitive injection of medication in hospital environments. Optionally, an untrained person may be enabled to inject himself in case of emergency. Emergency situations which may require such an injector may include, for example, in the army, to counter effects of chemical agents in case of chemical attacks and/or for administering pain killers and/or continues to counter animal bites with deadly poison and/or to treat an allergic reaction.

In some embodiments, an injector may automatically start injecting when the device hits a subject. In some embodiments, an operator may not need to hold the injector on the area to be injected surface during injection. For example, the device may be configured to inhibit pulling the device off the subject in a moment of panic and/or for other reasons that might bring an operator to pull the needle out of the patient too soon and/or before the medication was injected fully. In some embodiments, a device may be designed to alert multiple operators of previous injections, their time and/or their dosage. Alerting operators may inhibit multiple injections from different helpers that may lead to an over dosage. Alerting operators may inhibit the general problem of not knowing what medications has the patient received until the given moment which for example prevent an operator for administering a needed medicine and/or under dosing the subject.

An auto-injection device 100 of the present invention will be described in the following part in regard of the figures. It is a purpose of some embodiments of the invention to offer a new and inventive solution for an auto-injection device 100 which will solve the problems of some previous existing such devices. In some embodiments, the device will inhibit mistakes when using the auto-injection device 100. For example, some utilization mistakes that may be inhibited include: an operating pulling the injector away from an injection site too early and/or not giving the device enough time to inject the medicine, misplacing the device after use and/or not informing medical personnel subsequently treating the subject about the contents and/or timing of the injection. In some embodiments the current invention will inhibit removal of the device from an injection site before the injection is finished. In some embodiments the current invention will facilitate personal treating the patient afterwards to find the device and know when, how much and/or what was already injected into the patient. In some embodiments, the current invention will protect the medicine stored inside an injector from inside from external influences, for example water, dust, shock and/or temperature changes.

DETAILED EMBODIMENTS

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

FIG. 1 is a flowchart illustration of a method of administering a pharmaceutical in accordance with an embodiment of the present invention. In some embodiments, an injector is supplied 2700 in a compact storage configuration. For example, the storage configuration may have a flat form, for example the compact storage configuration may conveniently fit into a handbag and/or a pocket.

In some embodiments, the width of the device ranges for example between 2 to 5 cm and/or between 5 to 10 cm and/or between 10 to 20 cm and/or between 20 to 40 cm. Optionally, in the storage configuration, the height of the device ranges for example between 1 cm to 3 cm and/or between 3 to 6 cm and/or between 6 to 15 cm. For example, the height of the device may be perpendicular to a contact surface. Optionally, in the storage configuration, the device may have a disk shape.

In some embodiments, a pharmaceutical device will be prepared for administration via removal 2705 of a protective cover. For example, the cover may cover a contact surface and/or an adhesive surface of the device. Optionally, removing 2705 the cover will also remove a needle sleeve and/or a prime the device. Optionally, the cover will also protect the device from water, for example to IEC 60529 IP64 and/or IP67 standards.

In some embodiments, when the device is primed for injection from the storage configuration the device expands 2707. For example, the height of the device may increase by between 5 to 15% and/or between 15 to 30% and/or between 30 to 60% and/or between 60 to 200%. For example, the height of the device may expand 2707 by a telescoping mechanism. Optionally, expansion 2707 is powered by a stored energy source, for example an elastic member such as a spring. In some embodiments, when the device expands 2707 an injection needle moves from a storage angle (e.g. lying at low angle along the contact surface of the device) to an injection angle (e.g. at a higher angle with the contact surface ready to penetrate an injection site). Optionally the storage configuration and/or in the primed configuration, a needle tip is protected inside a housing of the device and/or does not present a stick hazard.

In some embodiments, the device injector is used 2770 to administer a pharmaceutical. For example, in the primed state, the contact surface of the injector may be placed against an injection site. Optionally, the contact surface is on a distal end of the injector. For example, the device may be activated by pushing a proximal surface of the device towards the contact surface. Optionally, when the user pushes past a threshold force and/or a threshold position, the injection needle tip is extended through a hole in the contact surface and/or inserted into the injection site and/or a pharmaceutical is discharged through the needle. Optionally, needle insertion is powered by a stored energy source for example a flexible energy storage device (e.g. a spring). After discharge of a dose of the pharmaceutical, the needle is optionally protected. For example, the needle tip may be retracted back into the housing of the device.

In some embodiments once the device has expanded 2707, it locks permanently and/or remains 2780 in the expanded configuration. For example, the device may remain at between 90 to 100% of its maximum height and/or between 75 to 90% and/or between 50 to 75%. For example, the device may lock in a height increase by between 5 to 15% and/or between 15 to 30% and/or between 30 to 60% and/or between 60 to 200% of the height of the storage configuration. Optionally, after use a needle is locked in a protected position. For example, the locked injector may be safe for disposal in municipal waste.

Figure 2:
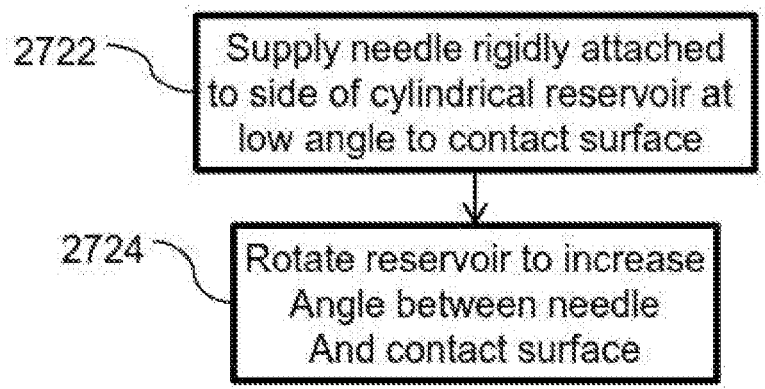
FIG. 2 is a flowchart illustration of a method of priming a pharmaceutical injector in accordance with an embodiment of the present invention.

FIG. 2 is a flowchart illustration of a method of priming a pharmaceutical injector in accordance with an embodiment of the present invention. In some embodiments, an injector is supplied 2722 in a compact form. For example, the height of the injector may be reduced by angling an injection needle to be at a low angle (for example parallel or at a finite angle as described above) to a contact surface on a face of the device. Optionally the needle is rigidly attached to a pharmaceutical reservoir. When the device is primed, the reservoir and needle may be rotated 2724, for example the rotation may direct the needle at a higher angle to the contact surface for example ready for insertion into an injection site. Additionally or alternatively, rotating the reservoir may align a point of the needle with a needle opening in the contact surface. Optionally, rotation of the reservoir is around a longitudinal axis thereof. For example, the needle may be rigidly attached to the reservoir and/or at an angle to the axis of the reservoir. For example, the angle between the needle and the longitudinal axis of the reservoir may range between 85 to 90 degrees and/or between 75 to 85 degrees and/or between 60 to 75 degrees and/or between 30 to 60 degrees.

Figure 3A:
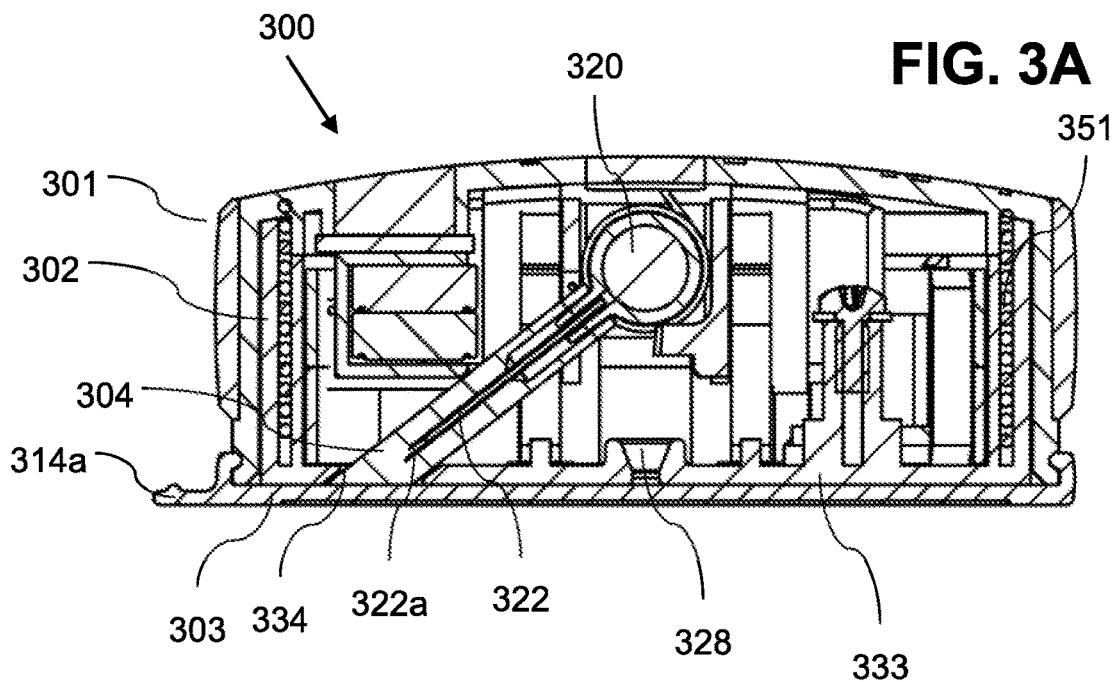
FIGS. 3A and 3B are schematic side cross sectional views of a pharmaceutical injector in a storage and primed configuration respectively in accordance with an embodiment of the present invention.
Figure 3B:
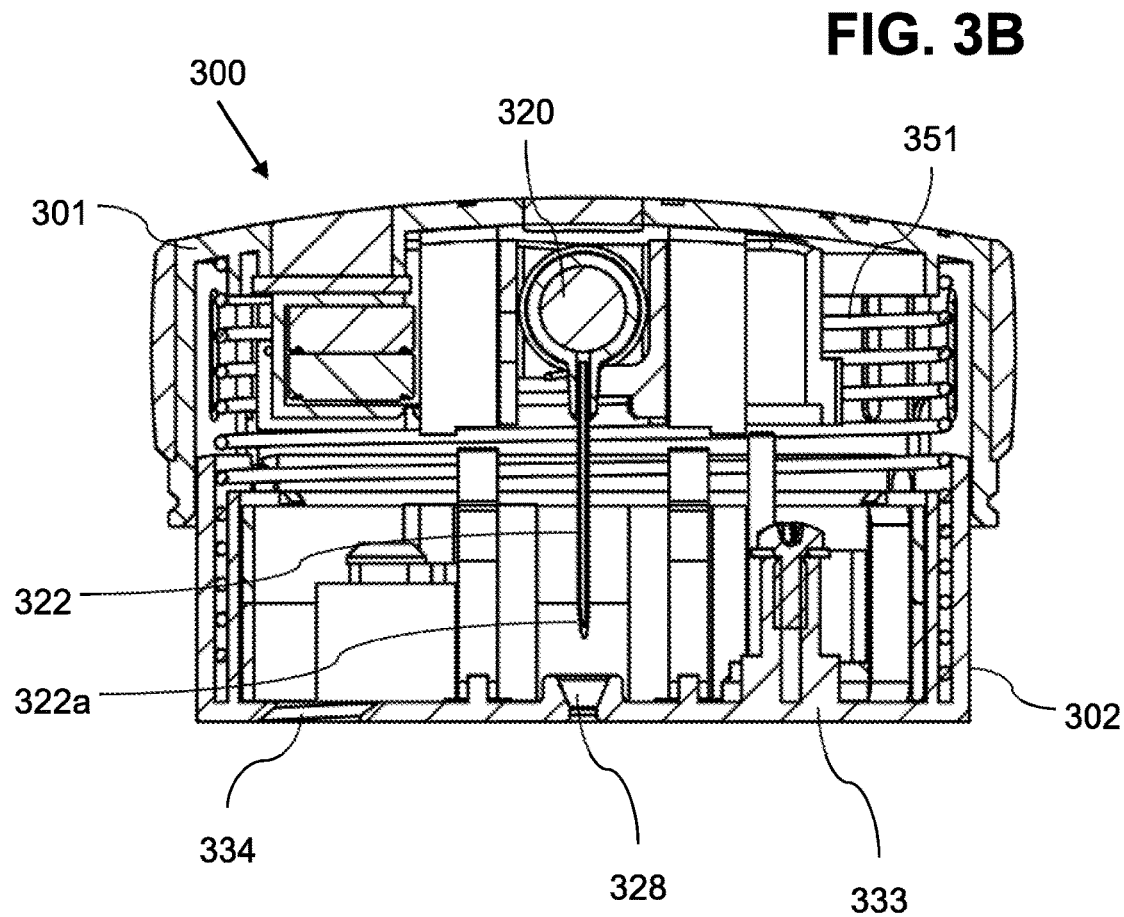

FIGS. 3A and 3B are schematic sides views of a pharmaceutical injector 300 in a storage and primed configuration respectively in accordance with an embodiment of the present invention. In some embodiments, an injector includes a contact surface 333 configurated for placement against an injection site. Optionally, in the storage configuration the height of injector 300 perpendicular to surface 333 is small compared to the width and/or area of the surface 333 (e.g. the injector has a thin flat form). A long injection needle 322 is optionally fit into the injector in the storage configuration at a low angle to surface 333. Optionally, the point 322a of needle 322 may not be aligned to a needle opening 328 in the storage configuration. For example, the needle may be held in place at the low angle by the lower housing 302 pressing against the distal end of needle 322. Alternatively or additionally, there may be a feature that protrudes from the lower body that holds the needle in the appropriate position. Optionally the protrusion is shaped to spread the stress and/or prevent bending of the needle. Optionally, when the injector 300 is primed, the height of the injector 300 is increased and/or the needle 322 is rotated to a higher angle with surface 333 and/or tip 322a is aligned with opening 328 (for example as illustrated in FIG. 3B). Optionally opening 328 is in a central portion of surface 333. For example, opening 328 may be in the center and/or in the central 10% and/or the central 30% and/or the central 60% of the width and/or breadth of surface 333. Optionally, needle 322 is rigidly attached to a pharmaceutical reservoir 320. Optionally, needle 322 and reservoir 320 rotate together.

In some embodiments, an injector 300 is biased to an expanded configuration by a stored energy source, for example a spring 351. Optionally, when a cover 303 is removed, the injector 300 expands spontaneously to the primed state. For example, a housing of the injector may be comprised of telescoping components including for example an upper casing 301 and a lower casing 302. Optionally, cover 303 holds the upper casing 301 and lower casing 302 in the collapsed, storage configuration. For example, cover 303 is attached to upper housing 301 and covers surface 333 of housing 302 preventing the two from moving apart. Peeling cover 303 off the injector optionally allows spring 351 to push apart upper casing 301 and lower casing 302, telescoping the injector into an expanded configuration. For example, cover 303 may be attached to housing 301 and/or 302 by means of tongue in groove and/or an adhesive and/or a friction fit and/or threading and/or another method. Optionally, cover 303 includes a peel tab 314a. In some embodiments, peel tab 314a makes it easier and/or more intuitive to peel off cover 303.

In some embodiments, cover 303 is attached to a needle sleeve 304. For example, when cover 303 is removed needle sleeve 304 is pulled off needle 322, and/or needle sleeve 304 is pulled through a hole 334 in surface 333. Optionally, reservoir 320 and/or needle 322 are biased to the upright orientation of FIG. 3B. Optionally cover 303 retains needle sleeve 304 and/or needle 322 and/or reservoir 320 in the reclining orientation of FIG. 3A while cover 303 is attached to injector 300. For example, when cover 303 is removed, needle sleeve 304 and/or needle 322 and/or reservoir 320 spontaneously revert to the upright orientation of FIG. 3B. Optionally needle sleeve 304 includes an extension 308. For example, extension 308 may be used to pull extension 308 off needle 322 before injection. For example, extension 308 may be connected to cover 303 such that when cover 303 is removed from the injector, needle sleeve 304 will come off with cover 303.

FIGS. 4A-4B are schematic side cross sectional views of a pharmaceutical cartridge in accordance with embodiments of the present invention. In some embodiments pharmaceutical reservoir 320 is rigidly attached to injection needle 322. Optionally, needle 322 and reservoir 320 are in fluid communication such that driving plunger 323 into the reservoir 320 drives a pharmaceutical out needle 322. Optionally, reservoir 320 may be open on opposite ends, for example the pharmaceutical may be driven out by driving two plungers into opposites ends of the reservoir 320 simultaneously. Alternatively or additionally, a reservoir 320' may be open only on one end (for example as illustrated in FIG. 4C). Optionally, an extension extends the closed end of the reservoir (for example making the cartridge more symmetrical around the needle 322 and/or facilitating mounting needle 322 in the center of the contact surface 333.

In some embodiments, needle 322 may protrude at an angle to the axis of the reservoir 320. Optionally a reservoir open only one end may have the needle 322a projecting from near the closed end of the reservoir. Alternatively or additionally, a needle may project from near the open end and and/or a middle portion of the reservoir. Optionally a cartridge may have an extension for extending the cylindrical shape of the reservoir. For example, when the needle protrudes near the closed end of the reservoir, the extension may add to the closed end such that the needle is in a middle portion of the cylindrical portion of the cartridge. Optionally, in FIGS. 4A-4C needle 322 is substantially perpendicular to the axis of the reservoir. In some embodiments the needle is attached to a side wall of the syringe and/or in a central portion of the syringe (for example as illustrated in FIGS. 4A and 4B). Alternatively or additionally, the needle may be attached near an end of the syringe (for example as illustrated in FIG. 4C). Optionally reservoir 320 may include a flange on one end and/or be filled like a standard prefilled syringe. Functionally, reservoirs 320 and/or 320' may work with injector 300 in a similar way.

FIG. 4C is a schematic exploded view of a cartridge assembly in accordance with an embodiment of the current invention. Optionally an elastic member (e.g. torsion spring 344) presses against needle 322 and/or a bracket 346 to bias the cartridge to an upright configuration. Optionally, two separate brackets 346 fit to opposite sides on reservoir 320 for example to simplify assembly of the cartridge into the injector 300. Also illustrated in FIG. 4B are locking cylinders 348. In some embodiments cylinders 348 are used to lock the cartridge in an extended and/or retracted position within the housing of injection 300 for example as described herein below.

Figure 5A:
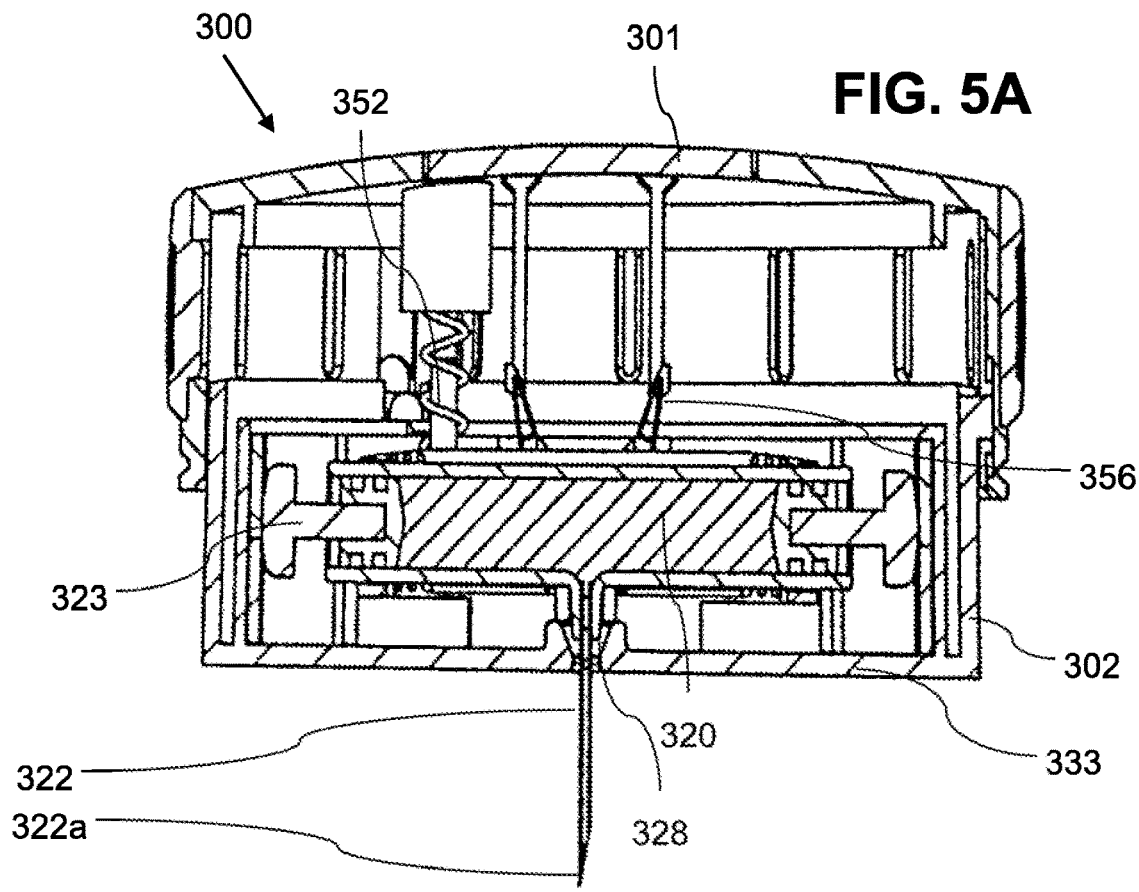
FIGS. 5A and 5B are schematic side cross sectional views of a pharmaceutical injector in an engaged and retracted configuration respectively in accordance with an embodiment of the present invention.
Figure 5B:
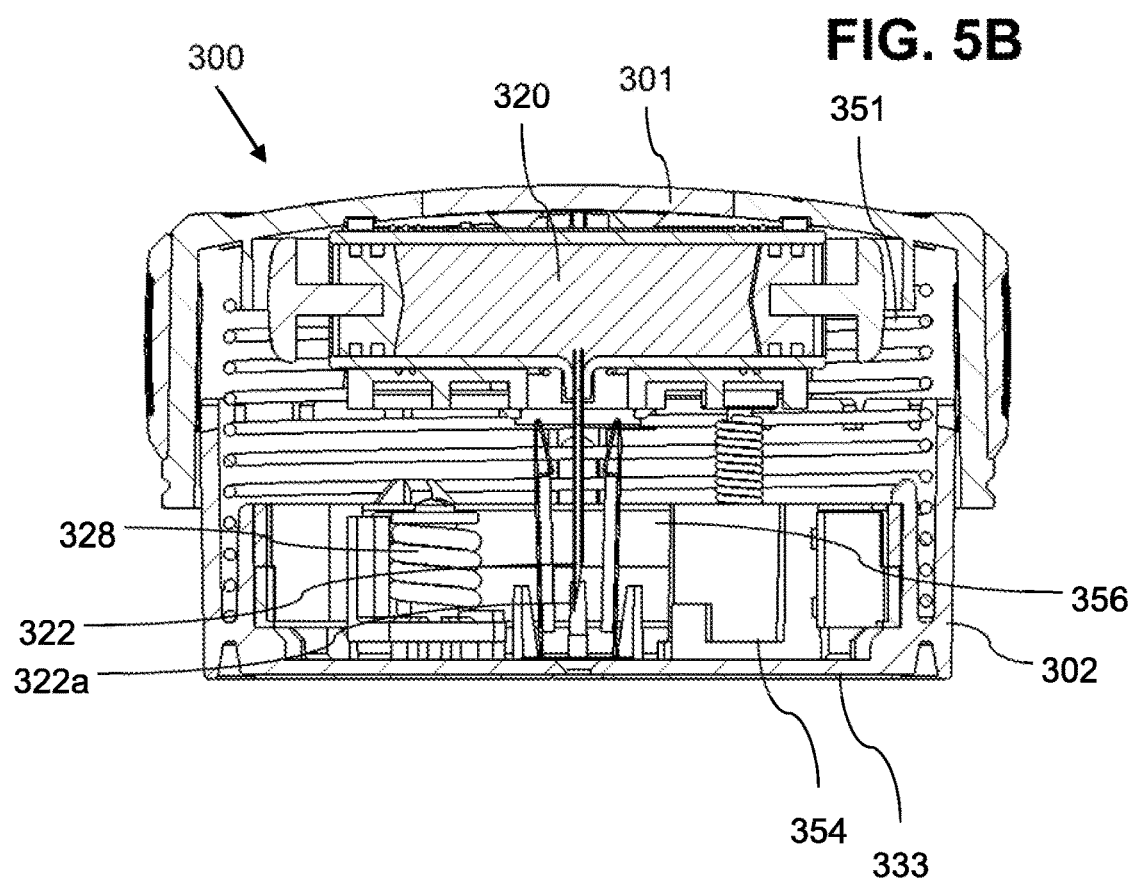

FIGS. 5A and 5B are schematic side cross sectional views of a pharmaceutical injector in an engaged and retracted configuration respectively in accordance with an embodiment of the present invention. In some embodiments, when injector is activated, tip 322a of needle 322 extends out opening 328 into an injection site. For example, injector 300 may be held to an injection site in a primed configuration (for example as illustrated in FIG. 3B) (note that the view of FIGS. 3A and 3B [viewing reservoir 320 end on] is rotated 90 degrees with respect to the view of FIGS. 5A and 5B [viewing reservoir 320 from its side]). When the injector in engaged, needle tip 322a is optionally extended out opening 328. For example, the cartridge (including for example reservoir 320, needle 322 and/or plungers 323) may be forced downward inside of the housing extending a distal portion of needle including tip 322a out opening 328.

In some embodiments, the cartridge may be biased to the extended position (for example, by an elastic element (for example a coil spring 352). Optionally in the primed state the cartridge may be locked in an un extended position, for example by an interference element 356. Optionally, when the injector is activated, interference element 356 is released and/or the cartridge is forced to the engaged position (for example as illustrated in FIG. 5A). For example, interference elements 356 may be released when an operator pushes the upper housing 301 towards lower housing 302 past a threshold position. In some embodiments discharge of the pharmaceutical starts automatically once the injector has reached the engaged configuration. Alternatively, or additionally, there may be an additionally activation step (for example triggered by an operator and/or depending in a sensor).

In some embodiments, after a dose of a pharmaceutical has been discharged, needle tip 322a is protected. For example, needle 322 may be retracted, for example as illustrated in FIG. 5B. Optionally retraction is powered by stored energy for example in an elastic element (e.g. a coil spring 354). For example, when injection ends, locking cylinders 348 may be rotated, releasing the cartridge to retract back up into upper housing 301. Optionally, before retraction, coil springs 352 are released to a neutral condition such that retract does not require overcoming resistance of spring 352. Alternatively or additionally, springs 352 may not be neutralized and/or springs 354 may be stronger than springs 352 overcoming the resistance of springs 352 to retract the cartridge.

Figure 6:
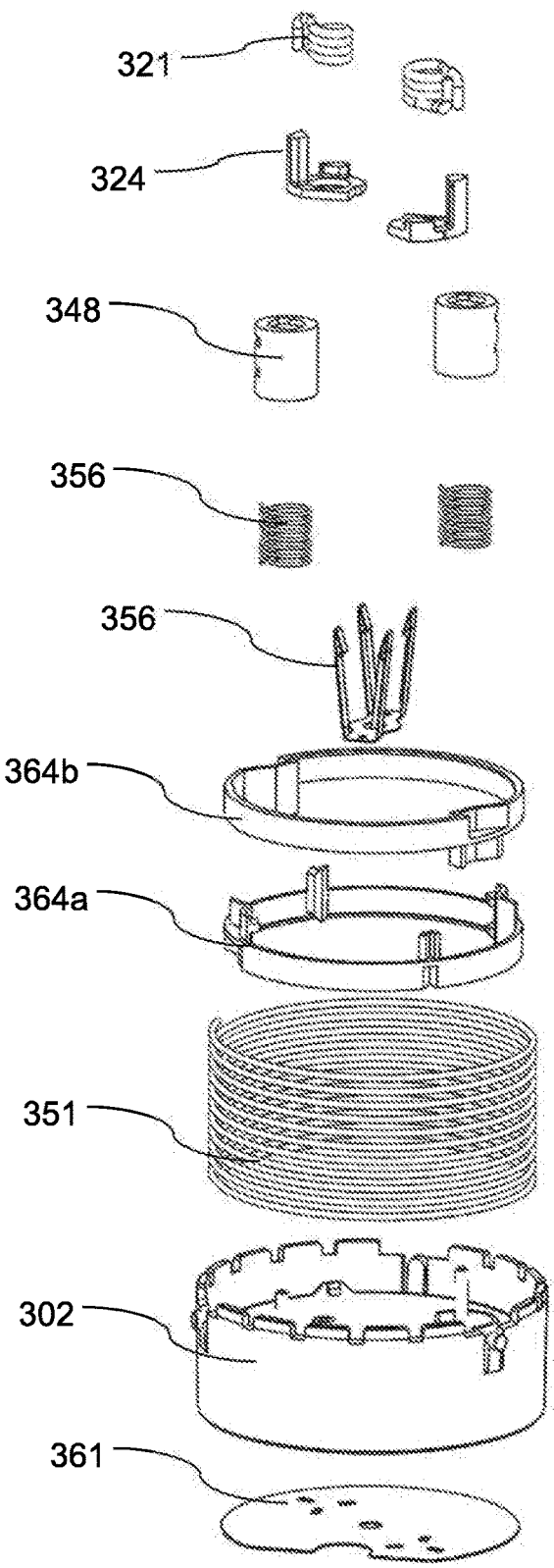
FIG. 6 is a schematic exploded view of an insertion—retraction mechanism of a pharmaceutical injector in accordance with an embodiment of the present invention.
Figure 8A:
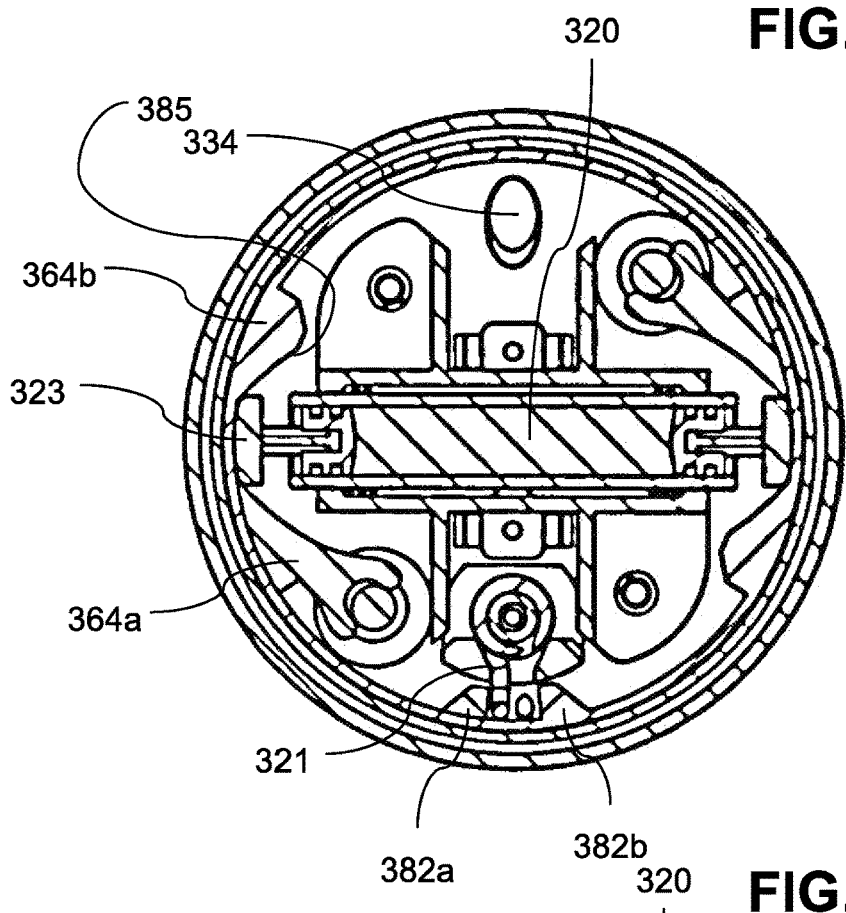
FIGS. 8A and 8B are schematic birds eye views of a discharge mechanism of a pharmaceutical injector before and after discharge respectively in accordance with an embodiment of the present invention.
Figure 8B:
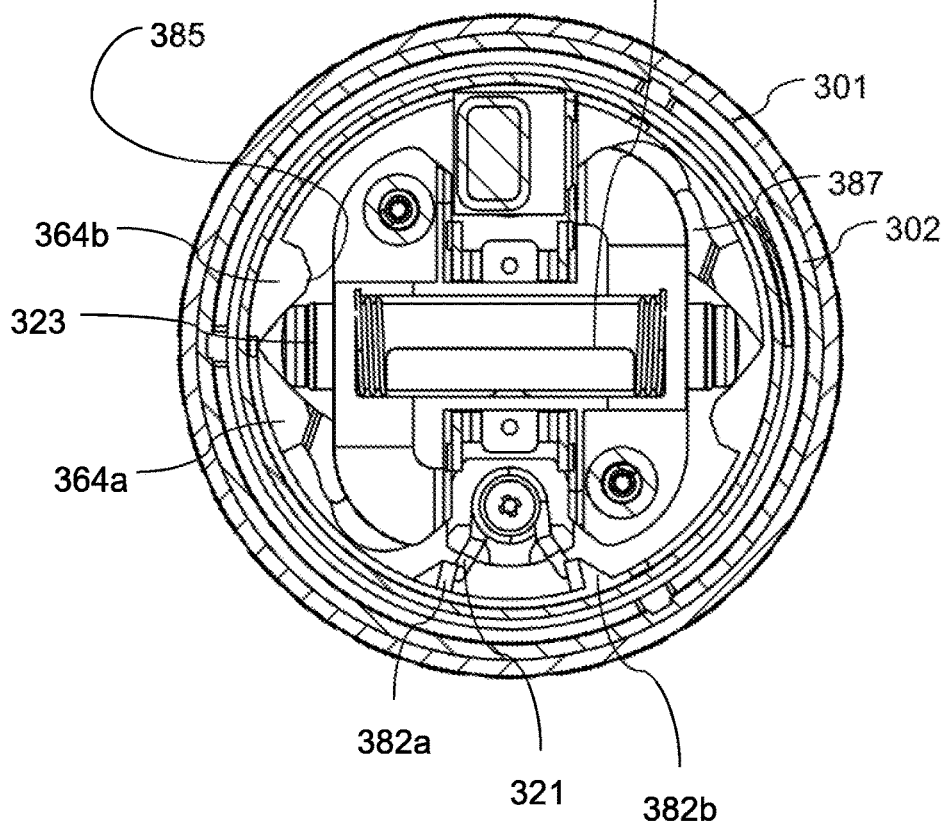

FIG. 6 is a schematic exploded view of an insertion retraction mechanism of a pharmaceutical injector in accordance with an embodiment of the present invention. In some embodiments discharge of a drug is via a rotary mechanism. For example, drug discharge and/or needle retraction may be driven by rotation of one or more rings 364a, 364b. rings 364a, 364b are optionally coaxial to the housing of the injector. Optionally, an elastic element, for example a spiral torsion spring 321, drives discharge of the medicine and/or rotation of the rings 364a and 364b, for example as illustrated in FIGS. 8A and 8B. Optionally, the contact surface 333 is covered by an adhesive 361. For example, adhesive 361 may be covered by cover 304 until the cover 304 is removed and then adhesive 361 may be used to adhere surface 333 to an injection site (for example on the skin of a subject). Also shown in FIG. 8 are two clips 324. For example, springs 321 may be wound and retained by clips 324 to store the stored energy before insertion into device 300. The spring 321 and clip 324 are optionally installed together into the injector 300. When the user activates the device (for example by pushing downward/distally on upper housing 301) clips 324 are released and torsion spring 321 begins to unwind driving discharge and/or eventually triggering needle retraction for example as illustrated and explained in regards to FIGS. 8A and 8B.

Figure 7:
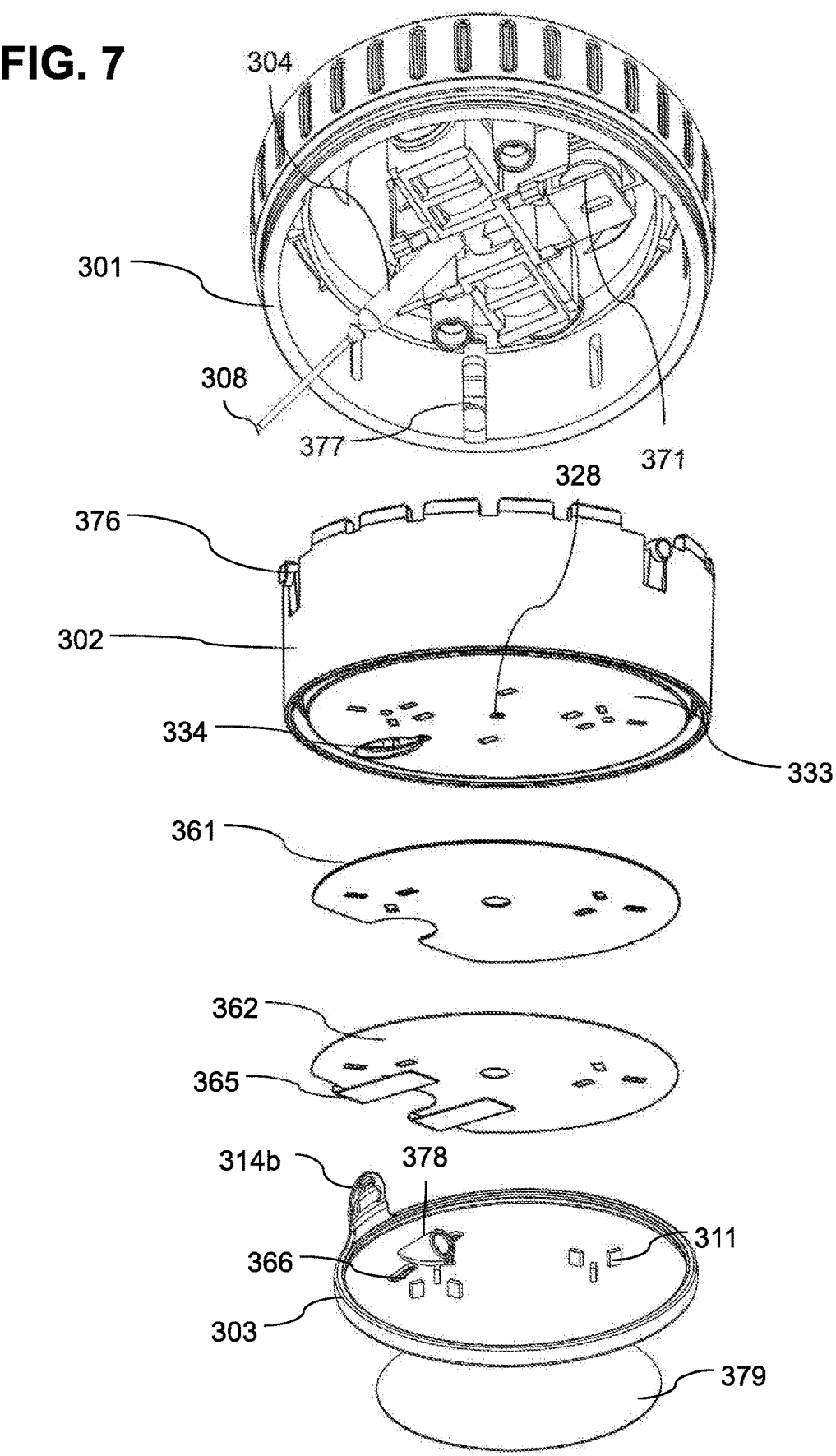
FIG. 7 is a schematic exploded view of a housing of a pharmaceutical injector in accordance with an embodiment of the present invention.

FIG. 7 is a schematic exploded view of a housing of a pharmaceutical injector in accordance with an embodiment of the present invention. Optionally, the adhesive layer 361 includes a double-sided adhesive 361 positioned between a cover 303 and a contact surface 333. Optionally, a lock between the upper housing 301 and lower housing 302 locks the injector into the expanded configuration when the device is primed before delivery of the pharmaceutical. For example, the lock includes an interference element 376 and/or a track 377. Optionally device 300 includes an indicator for example to show medics what dosage was given to the subject and/or when. For example, the indicator may include a timer 371.

In some embodiments, a proximal face of double-sided adhesive 361 is adhered to contact surface 333 on a distal end of lower housing 302. Optionally, a distal face of double-sided adhesive 361 is adhered to a proximal surface of cover 303. For example, cover 303 may be made of silicone, rubber and/or plastic that reversibly adheres to adhesive 361. For example, when cover 303 is removed the proximal face of adhesive 361 will remain attached to surface 333 and the distal face will be uncovered and ready to adhere to an injection site. In some embodiments the proximal face of cover 303 may be coated with a non-stick substance (for example Teflon and/or Kevlar). For example, cover 303 may protect the distal side of adhesive 361 and/or keep it fresh from attachment to an injection zone. Alternatively or additionally, the distal face of adhesive 361 may be covered by an adhesive protector sheet 362 (for example a sheet of Teflon and/or Kevlar). Optionally an edge and or a tab 365 of the protector sheet 362 is attached to cover 303 and/or inserted through a slit 366 in cover 303. Optionally sheet 362 is peeled off with cover 303. For example, the protector sheet 362 may protect the distal side of adhesive 361 and/or keep it fresh from attachment to an injection site. Optionally, when cover 303 is removed from injector 300, the protector sheet is peeled off adhesive 361. Cover 303 optionally includes a tab 314b for peeling. Optionally, cover 304 includes pins 311. For example, pins 311 may block activation of a discharge mechanism until cover 304 is removed.

In some embodiments, an injector may leave a mark on the subject for example to notify medical personnel what medicine the subject received. For example, ink may be placed on the contact surface (for example in a portion the adhesive) such that when the device is removed from the subject the injected medicine and dosage is imprinted on the injection site.

In some embodiments, when the injector is primed, the injector 300 is permanently locks in an expanded configuration. For example, interference element 376 locks to track 377.

In some embodiments, timer 371 is attached to a window in the proximal face of upper housing 301. For example, when the device is primed and/or activated, the timer may start counting. Optionally, injector 300 would then remain on the subject and/or the timer would give a visible sign to rescue workers when the subject received the pharmaceutical. Alternatively or additionally, a pharmaceutical administration device may include a removable indicator, for example a timer and/or a label. Optionally, the removable indicator is disconnected from the injector and/or attached to the subject for viewing by emergency and/or medical personnel during further treatment of the subject.

In some embodiments, a cover will include a connector 378. Optionally, during assembly of the injector connector 378 is attached to needle sleeve 304 in such a way that when cover 303 is removed from injector 300, needle sleeve 304 is pulled off needle 322 and/or out opening 334 and/or lower housing 302 is pushed away from upper housing 301 allowing needle 322 to move to an upright position and/or allowing needle tip 322a to align with needle opening 328. In some embodiments a label 379 is attached to cover 303.

FIGS. 8A and 8B are schematic birds eye views of a discharge mechanism of a pharmaceutical injector before and after discharge respectively in accordance with an embodiment of the present invention. In some embodiment, discharge of a pharmaceutical is driven by a plunger 323 being pushed into reservoir 320. Optionally, plunger 323 is pushed by a rotating rings 364a and/or 364b. For example, torsion spring 321 spreads due to elastic energy stored in the spring. Spreading of the spring optionally pressures apart tabs 382a and 382b on rings 364a and 364b. For example, each ring 364a, 364b includes an inclined surface 385 positioned such that when the ring 364a, 364b is rotated, the inclined surface 385 pushes a plunger 323 into reservoir 320. In some embodiments, one or more plungers 323 may be driven into a reservoir to release a dosage of a pharmaceutical without entirely emptying the reservoir 320 (for example as illustrated in FIG. 8B).

In some embodiments, movement of rings 364a and/or 364b may release a needle retraction mechanism. For example, a ring may include an extension 387 which in the pre-discharge configuration (for example the primed configuration as illustrated for example in FIG. 8A) may block needle retraction and/or in the configuration after discharge moves out of the way and/or releases the retraction mechanism (for example as illustrated for example in FIG. 8B). Alternatively or additionally, teeth on a ring may mesh with teeth on a locking mechanism for example rotating and/or unlocking the mechanism to cause needle retraction.

Figure 9A:
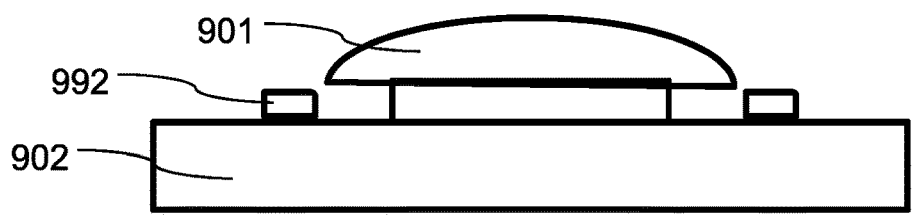
FIGS. 9A-9C are schematic side views of a pharmaceutical administration device before priming, after priming and after activation respectively in accordance with an embodiment of the present invention.
Figure 9B:
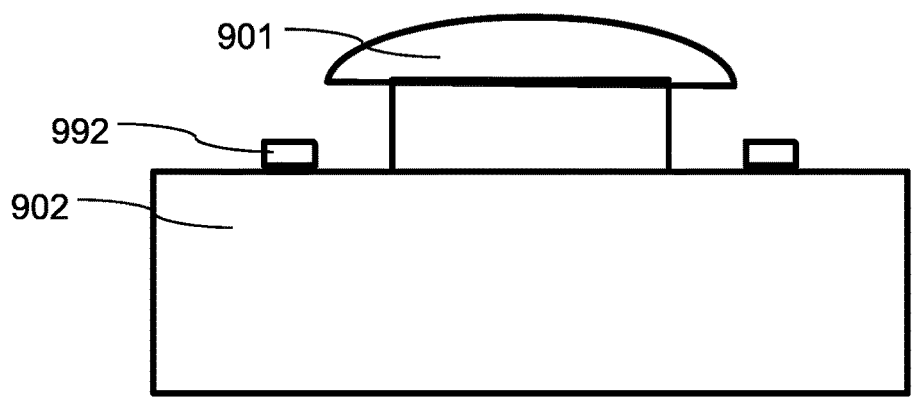
Figure 9C:
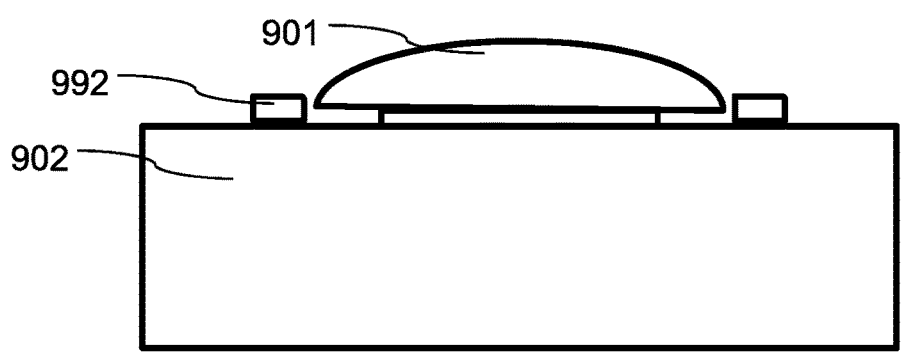

FIGS. 9A-9C are schematic side views of a pharmaceutical administration device before priming, after priming and after activation respectively in accordance with an embodiment of the present invention. In some embodiments, a button 901 may have a rounded top and/or an overhang, intuitively reminding an operator of an emergency button. In some embodiments, a housing 902 may have a round and/or oval and/or rectangular and/or combination cross section. Optionally, an activation button 901 may be rounded and/or dome shaped. Optionally the button 901 top is flat and/or mildly dome shape and/or is wide (for example with a width of between 2 to 4 cm and/or between 4 go 8 cm and/or between 8 to 16 cm). Optionally in a stored configuration, the button 901 is retracted for example as illustrated in FIG. 9A.

Optionally, when the device is primed the button may extend proximally for example as illustrated in FIG. 9B. In some embodiments, pushing the button 901 distally activates the device (for example causing needle insertion and/or drug discharge and/or afterwards needle retraction). Optionally, the button 901 is shaped for pushing with an open palm. Optionally when the button has been pushed the edges of the button are shielded, for example by a flange 992 protruding from the housing 902 of the device. Shielding the sides of the button after activation may inhibit a user immediately grasping the injector after injection and/or removal of the injector before the end of discharge.

Figure 10A:
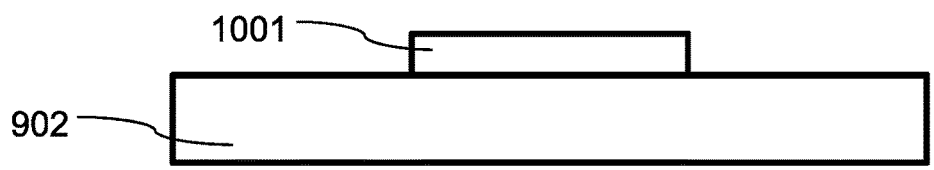
FIGS. 10A-10C are schematic side views of a pharmaceutical administration device before priming, after priming and after activation respectively in accordance with an embodiment of the present invention.
Figure 10B:
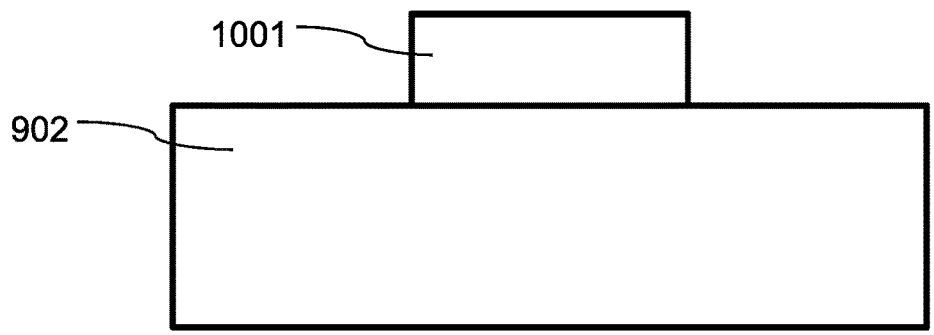
Figure 10C:
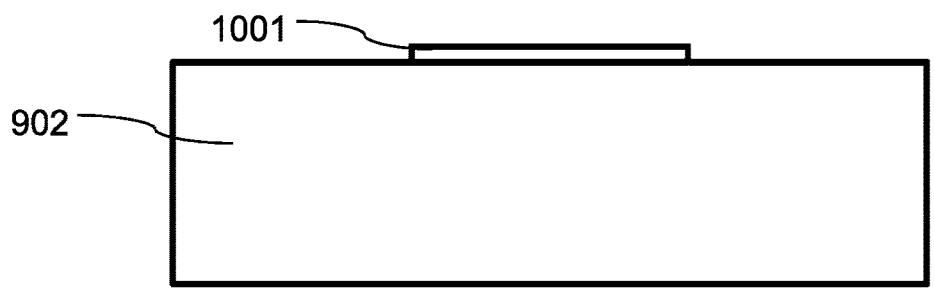

FIGS. 10A-10C are schematic side views of a pharmaceutical administration device before priming, after priming and after activation respectively in accordance with an embodiment of the present invention. Optionally, an activation button 1001 may have a cylindrical form. Optionally, when the button is depressed it sinks far enough into the injector that there is little side surface of the button to grasp inhibiting immediately pulling the injector back out away from the injection site. For example, at the end of pushing less than 1 mm of the height of the button may be exposed and/or less than 5 mm and/or less than 10 mm and/or less than 20 mm.

In some embodiments, an activation button may protrude through a hole in the housing of the device. Alternatively or additionally, the housing may be sealed. For example, the housing may include a soft area (for example made of elastomer) which is pushed to activate the device.

Figure 11:
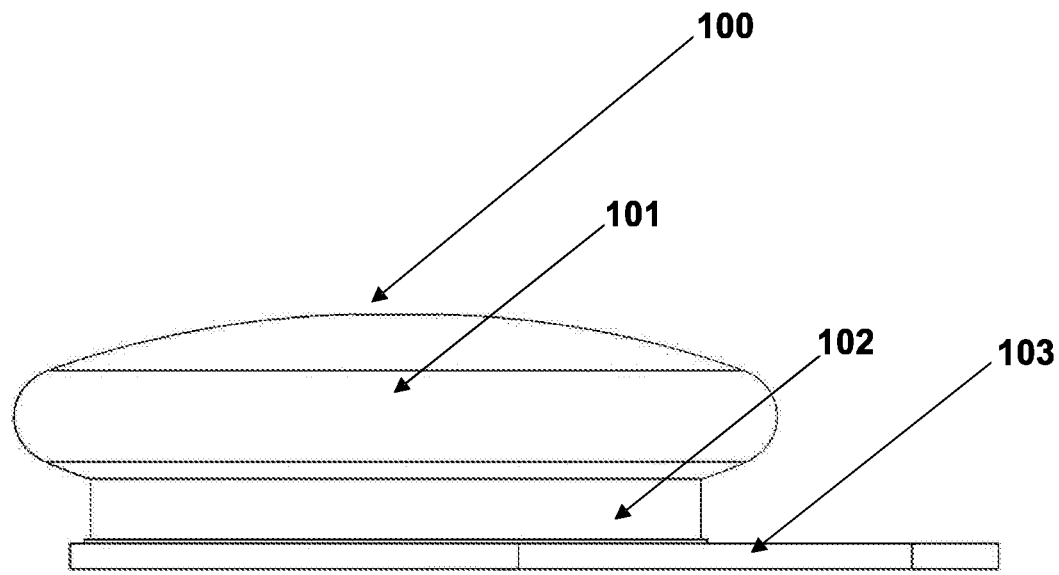
FIG. 11 is a perspective view of a first embodiment of an auto-injector 100 in accordance with an embodiment of the present invention.

FIGS. 11 to 24 illustrate a low-profile injector in accordance with an embodiment of the current invention. As seen in FIG. 11, an embodiment of a new and inventive auto-injector device 100 in a storage configuration has a form that is wider (in one, some and/or all lateral directions) than its height (along a proximal-distal axis). In some embodiments, the housing includes three components an upper housing 101, a lower housing 102 and/or a protective cover 103. Upper housing 101 is optionally flat and/or comfortably fits into an adult hand. The upper housing 101 may have a form that intuitively appears like a button that activates the auto-injection device 100. In some embodiments, the upper housing 101 and/or the rest of the housing have a circular cross section. Alternatively or additionally, they may have any form that would be suitable to house the injection module 150.

In some embodiments, the upper housing 101 has an opening (for example on one end thereof). The opening may interconnect with the lower housing 102. For example, together the upper housing 101 and lower housing 102 create a closed space. Components needed for the injection operation may be installed in the created space.

In some embodiments, the upper housing 101 and the lower housing 102 are movably connected to each other in such a way that when the upper housing 101 is pushed by the operator, it will be move distally towards the lower housing 102. For example, the lower housing 102 may slide into the upper housing 101 and/or the upper housing 101 may slide into the lower housing 102.

In some embodiments, the upper housing 101 is not necessarily directed vertically upward. For example, the upper housing may be on a proximal side of the device (e.g. towards an operator and/or away from a subject contact surface and/or away from an injection site). The lower housing 102 is not necessarily directed vertically downward. For example, the lower housing may be on a distal to the upper housing (e.g. towards a subject and/or towards a contact surface [e.g. the lower housing may include a contact surface for example for contacting skin and/or clothes of the subject of the injection] and/or towards an injection site).

In some embodiments, the third part of the housing includes a protective cover 103. Protective cover 103 is optionally attached to a portion of the upper housing. Alternatively or additionally cover 103 may cover and/or be attached to a portion of the lower housing 102, for example a portion which is not inserted into the upper housing 101. For example, cover 103 may be attached to and/or cover a distal end of the injector. In some embodiments, cover 103 is attached in a location and/or manner that allows the user to take it off without leaving any parts of cover 103 on the lower housing 102. Optionally, the protective cover 103 includes at least one part of it exceeds the boundaries of the housing in such a way that it is easy for the user to hold it and/or use that part to pull the cover 103 away from the lower housing 102. Optionally, while cover 103 is on the injector, the needle is shielded and/or the needle is prevented from being extended and/or the injector 100 is inhibited from being activated In some embodiments, the lower housing includes a contact surface. Optionally, the contact surface includes a flat surface and/or a gently curved (for example concave) to fit the skin of an injection zone on a subject. Optionally. at least part of the contact surface is covered with an adhesive layer 161. For example, the adhesive layer 161 may be located Between the lower housing 102 and the protective cover 103. In some embodiments, the adhesive layer 161 may serve one or more of a number of functions. For example, adhesive layer 161 may hold the protective cover 103 over the lower housing 102. Optionally, cover 103 is held in such a way that it fully seals any entry or exit into the auto-injection device 100. For example, adhesive layer 161 may attach the auto-injection device 100 to an injection site (for example a surface to which the drug will be injected). For example, adhesive layer 161 may prevent the injector from falling off and/or the adhesive may keep the injection zone clean and/or sterile and/or the adhesive layer may protect the injection site from potential contamination. In some embodiments, holding the auto-injection device 100 on the injected surface will inhibit losing the device. For example, when a medic sees the device on the injection site it may help him understand what happened to the patient. For example, the injector may include information about what, when and/or how much medicine was injected. For example, the adhesive layer may self-adhere the auto-injection device 100 on the injection site during discharge of a pharmaceutical. In some embodiments, self-adhering of the auto-injector to the injection site may simplify the utilization and/or free a hand of the operator and/or inhibit the user moving the injector in any way (for example proximally which may pull the needle out of the subject and/or laterally which may cause pain and/or damage to the injection site and/or the needle). For example, the operator may only have to apply device 100 onto the injection and activate device 100. Optionally, Between the lower housing 102 and the protective cover 103 a disinfectant material may be placed. The disinfectant optionally disinfects the injection site and/or preserves sterility of the adhesive and/or the contact surface. The disinfectant in optionally be mixed into the adhesive and/or may be placed separately on the contact surface and/or inside of the lower housing 102.

Figure 12A:
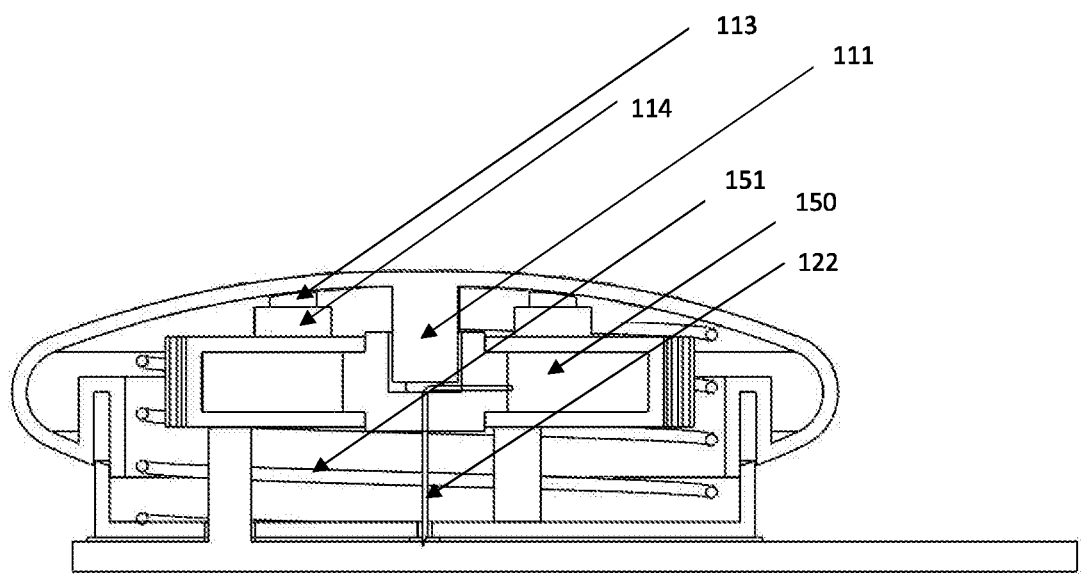
FIGS. 12a and 12b are cross-sectional side views of an auto-injector in a storage configuration in accordance with an embodiment of the present invention.
Figure 12B:
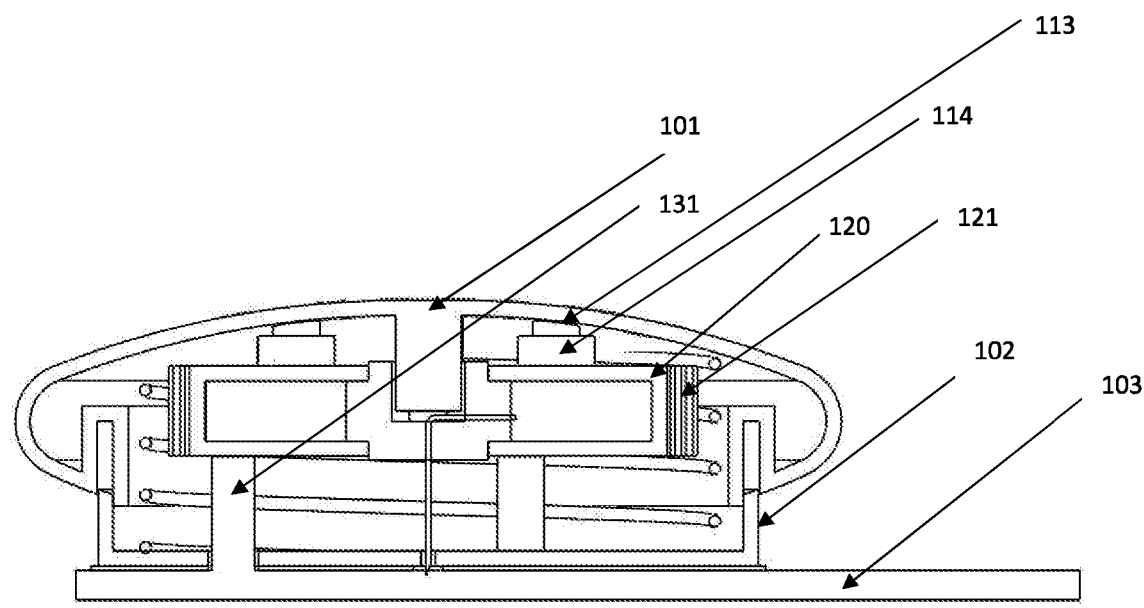
Figure 13:
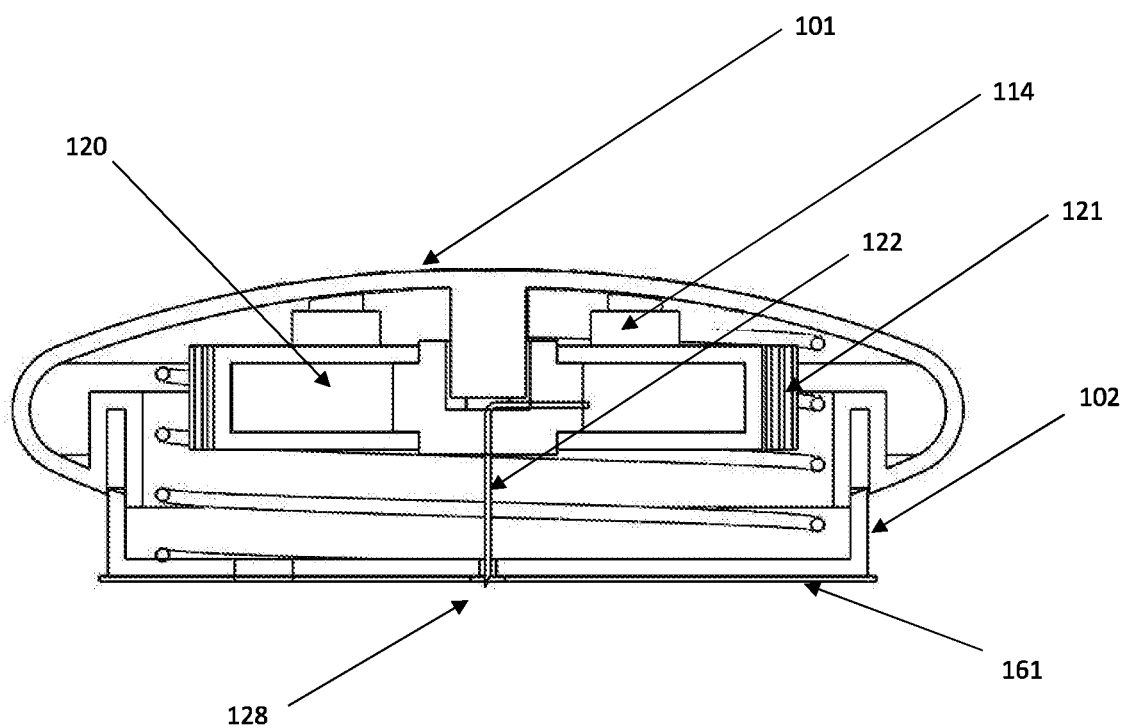
FIG. 13 is a cross-sectional side view of an auto-injector in a primed configuration after a protective cover has been removed in accordance with an embodiment of the present invention.

FIGS. 12a and 12b display a cross-sectional side view auto-injection device 100 in a storage configuration before activation. In this configuration, the auto-injection device 100 can be stored for a longer period of time. In this cross-sectional side view, it is possible to see components of an exemplar injection module 150 that may be used in some embodiments of the invention. Other injection modules may be used in place of and/or along with those illustrated in FIG. 12a. In some embodiments, all of the components will fit in the flat space created in the auto-injection device 100. In this implementation the injection module 150 comprises a flat drug reservoir 120 where the medication will be stored. Optionally, the drug reservoir 120 is connected to a medical needle 122. For example, the needle may be inserted into a subject and/or a pharmaceutical may be pushed out of the flat drug reservoir 120 through the medical needle 122 into the subject. Other injecting means may be used for example needle free injection and/or a catheter.

In some embodiments, a rotational spring 121 at least partially surrounds the drug reservoir 120. Optionally, energy stored in the rotational spring 121 pushes the medication from the drug reservoir 120 into the medical needle 122. Alternatively or additionally, another propulsion means may be used for this purpose.

Figure 17:
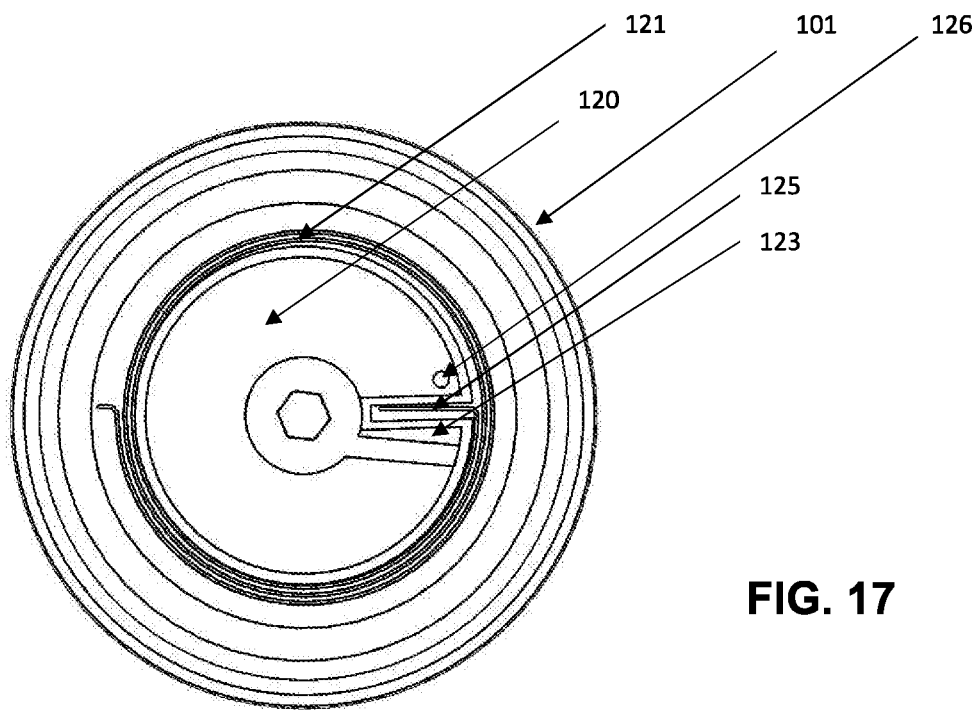
FIG. 17 is a cross-sectional bird-eye view of an auto-injector in accordance with an embodiment of the present invention in an almost empty configuration after—release of a drug.

FIG. 17 illustrates pushing a pharmaceutical out of a reservoir in accordance with an embodiment of the current invention. The drug reservoir 120 optionally comprises an air inlet 126 and/or a rotational spring slot 125 which can have a double function being also used as a fixed wall. The drug reservoir 120 optionally includes a moving wall 123 and/or plunger, which can be moved in a rotational move in the direction of the fixed wall 125 to create pressure on the medication and/or to push the medication through a needle and/or through an exit out of the drug reservoir 120.

In another implementation the drug reservoir 120 itself may be moved and/or the plunger 123 can be used as the fixed wall. A medical needle 122 is optionally installed in such a way that one side of it is connected into the drug reservoir and when the pressure is applied on the medicine it will be pushed into the medical needle 122. The air inlet 126 is optionally used to let air into the empty space formed after the medication was pushed out. In some embodiments, equalizing pressure may facilitate an even application of the force upon the medication and/or evenly pushing out of the medication from the drug reservoir 120 into the medical needle 122 and/or into the subject to be injected with the medication.

FIGS. 12a and 12b are cross-sectional side views of the auto-injection module illustrated in FIG. 11 in an unused first position. In some embodiments, upper housing 101 is interconnected with the lower housing 102. Optionally, a space in the upper housing 101 receives the walls of the lower housing 102. For example, the lower housing may 203 may move in relation to the upper housing 101. In some embodiments, the inside of the auto-injection device 100 sealed and protected from external factors like dirt and temperature changes. Alternatively or additionally, a wall of the upper housing 101 may fit into a space prepared in the lower housing 102.

In some embodiments, an elevating spring 151 is placed in the closed space, created in the housing. Other flexible materials may be used instead of and/or along with a spring. The elevating spring optionally holds the upper housing 101 and the lower housing 102 in place and connected to each other. The elevating spring 151 is optionally formed in such a way that it does not interfere with the injection module 150 placed in the closed space.

In some embodiments, the upper housing 101 includes a reservoir centering pin 111. Optionally pin 111 is inserted into the center part of the reservoir in such a way that it facilitates rotational movement. Additionally or alternatively, the upper housing 101 includes a rotation preventing pin 112 and/or the drug reservoir 120 has a rotation preventing socket 124. In a storage configuration of the injection module 100 the rotation preventing pins 112 is optionally sunk in the rotation preventing sockets 124 in such a way that they prevent the rotational move of the drug reservoir 120. For example, this counteracts the constant rotational force of rotational spring 121 on the drug reservoir 120. Optionally, pins 112 and sockets 124 prevent accidental moment and as such, pushing of the medication. Alternatively or additionally, pins 112 and the sockets 124 are optionally positioned to prevent movement of the plunger 123 in the implementation described above.

In some embodiments, the protective cover 103 includes a safety pin 131 and the lower housing 102 has at least one safety pin hole 132 through which the pin 131 can be inserted into the lower housing, in such a way that it exactly reaches the drug reservoir 120. The safety pin 131 optionally inhibits accidental activation of the auto-injection device 100 for example through an accidental pressure upon one side or both sides of the device.

In some embodiments, the activation and using of the auto-injection device 100 may include some or all of the following steps:

In some embodiments, the device is primed for use by removing protective cover 103 from the device. For example, while the device in a storage state cover 103 may be pulled away from the lower housing 102. An illustration of the device 100 without the protective cover can be seen in FIG. 13.

In some embodiments, an operator places the primed auto-injection device 100 onto an injection site. From example a skin contact surface that was exposed when cover 103 was removed may be placed on the injection site. The injection site is typically on the skin of a subject to whom the medication is to be administered [note that the subject himself may be the operator (self-injection) and/or the operator may be another individual]. Alternatively or additionally, the device 100 could also be placed directly on the garment or other material covering the skin. The adhesive layer 161 optionally attaches the device 100 to the injection site, for example in such a way that it will not fall off.

In some embodiments, the injector is activated by applying enough vertical power on the upper housing 101 that it is pushed down to a threshold location. A visual and/or a haptic and/or an audio signal may optionally be given to the operator as soon as the device upper housing 101 has reached the needed activation position. Optionally, certain pressure threshold can be installed in the device 100. For example, when pressure on the top of the device reaches a threshold, an automatic needle insertion mechanism may be triggered. Alternatively or additionally, the needle may be inserted directly by force of the operator's hand. In some embodiments, the adhesive layer 161 may be configured to hold the device to the skin strongly enough to prevent the device from falling from its own weight (e.g. from any orientation) and/or to counteract the force of the needle entering the skin of the subject and/or when subject to acceleration to do movement of the subject. For example, in some embodiments the adhesive layer 161 surrounds and/or is intended to hold the device strongly to the skin at the needle exit point 128 where the medical needle 122 exits into an injection site.

Figure 14:
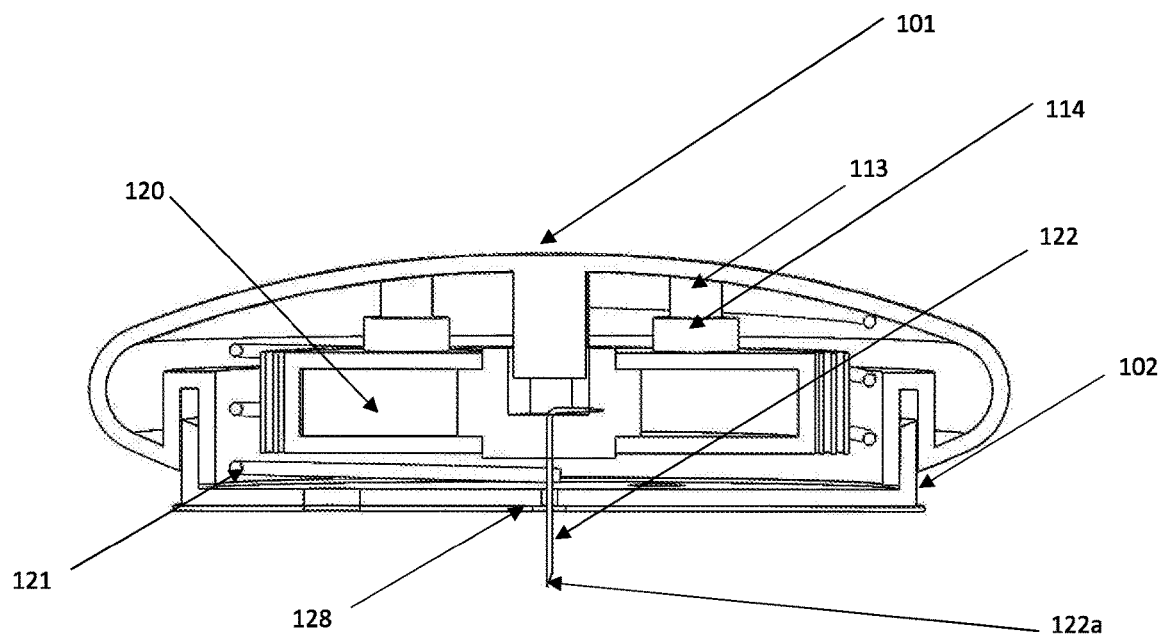
FIG. 14 is a cross-sectional side view of an autoinjector in accordance with an embodiment of the present invention in an activated configuration.
Figure 15:
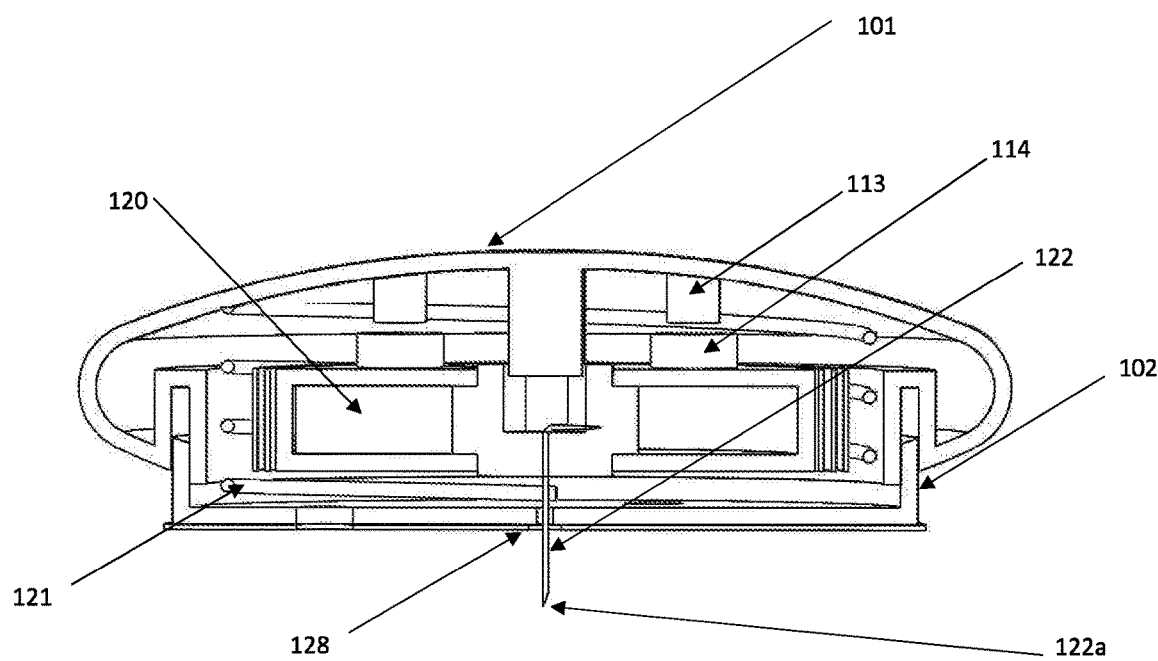
FIG. 15 is a cross-sectional side view of an autoinjector actively injecting a drug in accordance with an embodiment of the present invention after pressure has been released.

FIG. 14 illustrates the auto-injection device 100 in an activated state after the operator has applied enough pressure to overcome the threshold and activated the device. Optionally, after activation the medical needle 122 is pushed out of the device 100 and/or into the skin of the patient. For example, device 100 is built in such a way that the medical needle 122 will exit to penetrate the skin and reach a desired injection depth taking into consideration that a garment might be in between. Optionally, the moment the operator releases the device 100 and/or stops applying pressure upon it, the elevating spring 151 will push the upper housing away from the drug reservoir 120 so that the rotation preventing pins 112 will exit the rotation preventing sockets 124 and the rotational spring 121 is free to apply the stored energy on to the drug reservoir 120 which will start turning, thus activating and pushing the medication into the medical needle 122 and out into the patient. Other forms of preventing the accidental activation of the injection module. In some embodiments, (for example as illustrated here and/or in the embodiment of FIGS. 3-8 and/or any of the other embodiments illustrated herein) a skin sensor may detect when the contact surface is placed against the skin and/or prevent needle extension and/or pharmaceutical discharge when skin is not detected. For example, a skin detector may include a mechanical contact switch and/or an electrical detector (e.g. conductivity, capacitance etc.)

In a further possible implementation, the injection module will start injecting the medication during the time where the operator continues applying pressure on the device 100. Optionally, the injection module 150 will be activated after the needle 122 is inserted through the injection site and/or while the operator is still applying pressure on the device. For example, the preventing pins 112 will break through the power applied by the operator on the upper part 101. Other possibilities to start the injection during the time that the operator is applying pressure may be used. This may be useful in cases where the injection site will not support the weight of the device (for example when injecting through baggy clothes) and/or the operator continues applying the force to keep the device on the injection site. For such a case the device 100 may optionally have a further function for example a security needle to attach it on that surface after application of the injection so that it does not get lost. A further feature of some embodiments of the injection device 100 may include a strap stored in the casing which can be used to attach the injection device to a limb of a subject.

In some embodiments, after all the medication has been injected an activation display mechanism 170 displays the fact that the injection was activated. Optionally, a time display mechanism 171 may display the time and/or date of activation. The time display mechanism may use any part of the auto-injection device 100 as a display.

Figure 18:
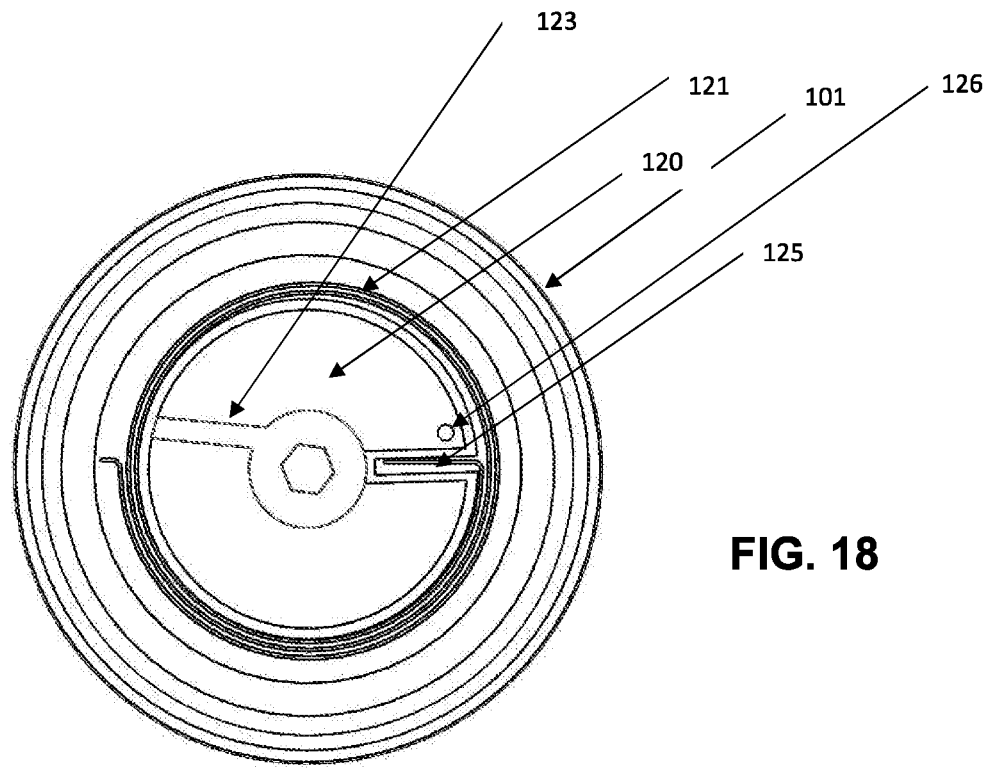
FIG. 18 is a cross-sectional bird-eye view of the auto-injector in accordance an embodiment of the present invention at half way position—after release half of the drug.
Figure 19:
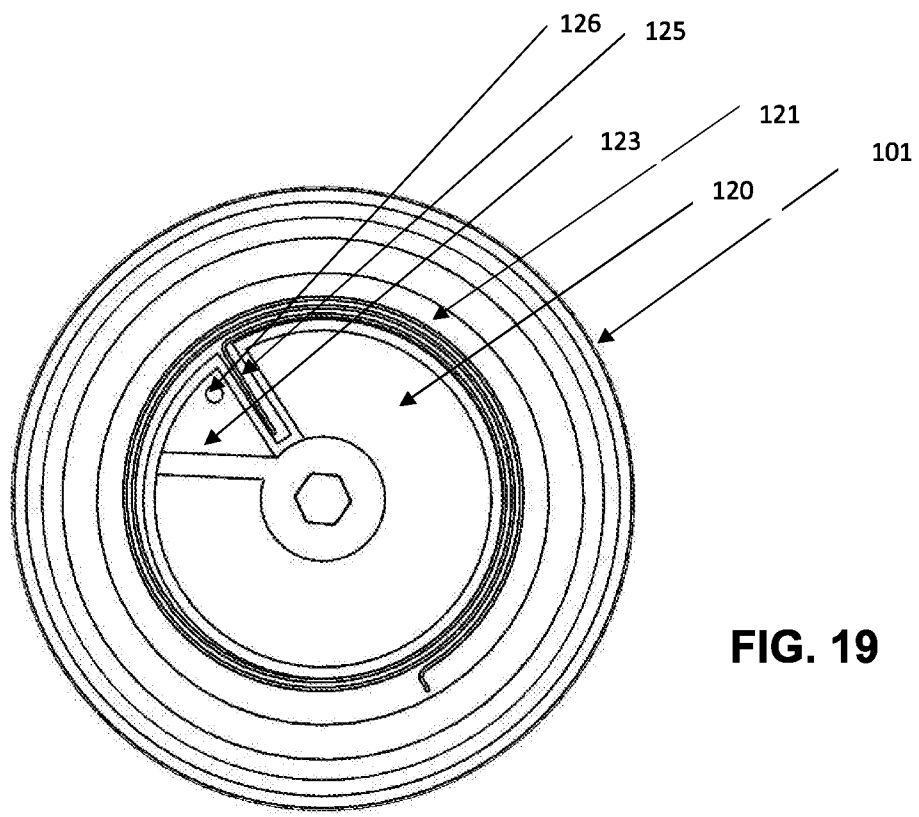
FIG. 19 is a birds-eye view of an auto-injector in accordance with an embodiment of the present invention at full position.
Figure 20:
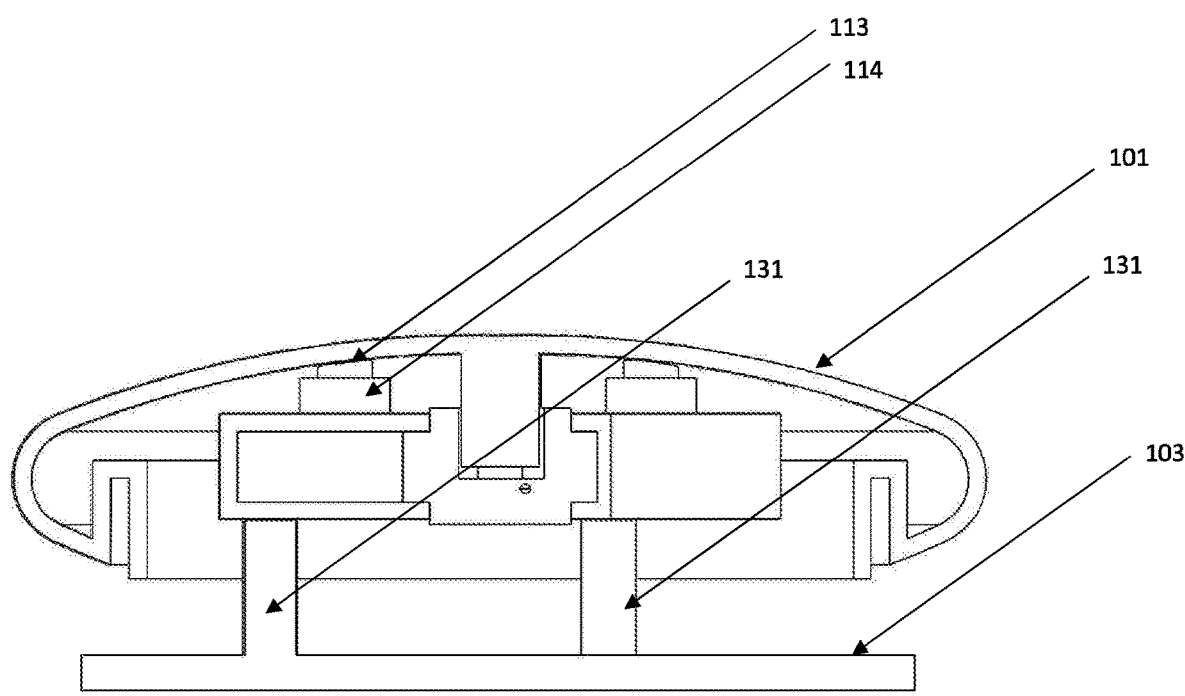
FIG. 20 is a cross-sectional view of safety pins in accordance with an embodiment of the current invention.
Figure 21:
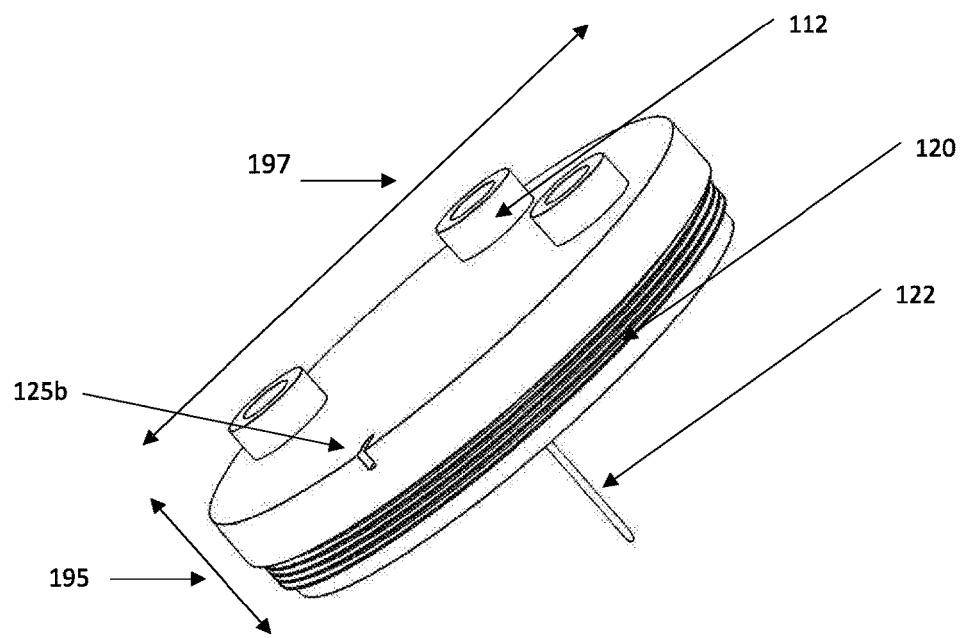
FIG. 21 is a view of an injection module in accordance with an embodiment of the present invention.
Figure 22:
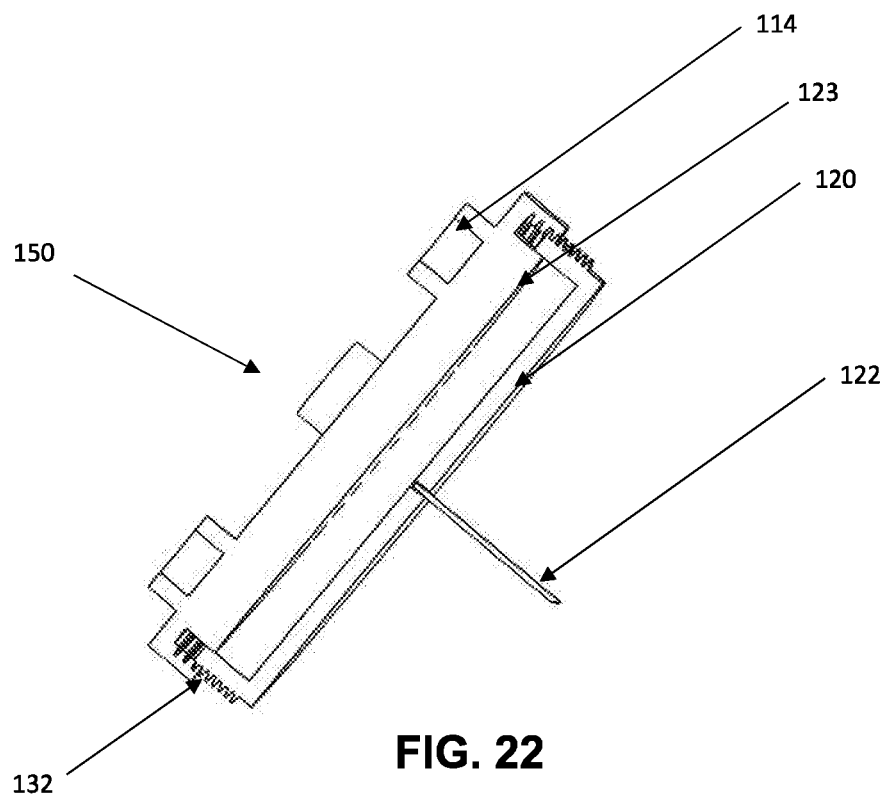
FIG. 22 is a cross-sectional view injection module in accordance with an embodiment of the present invention.
Figure 23:
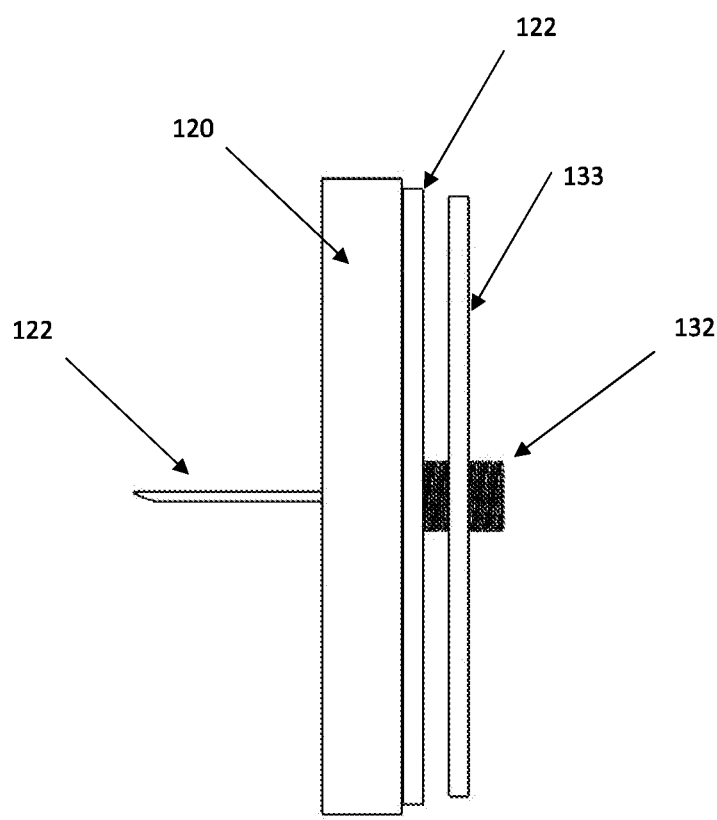
FIG. 23 is a view of an injection module in accordance with an embodiment of the present invention.
Figure 24:
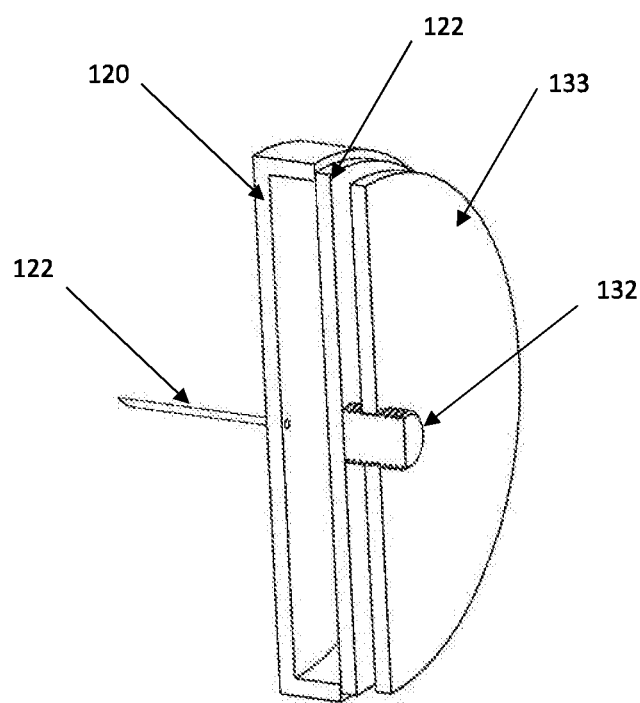
FIG. 24 is a cross-sectional view of an injection module in accordance with an embodiment of the present invention.
Figure 25:
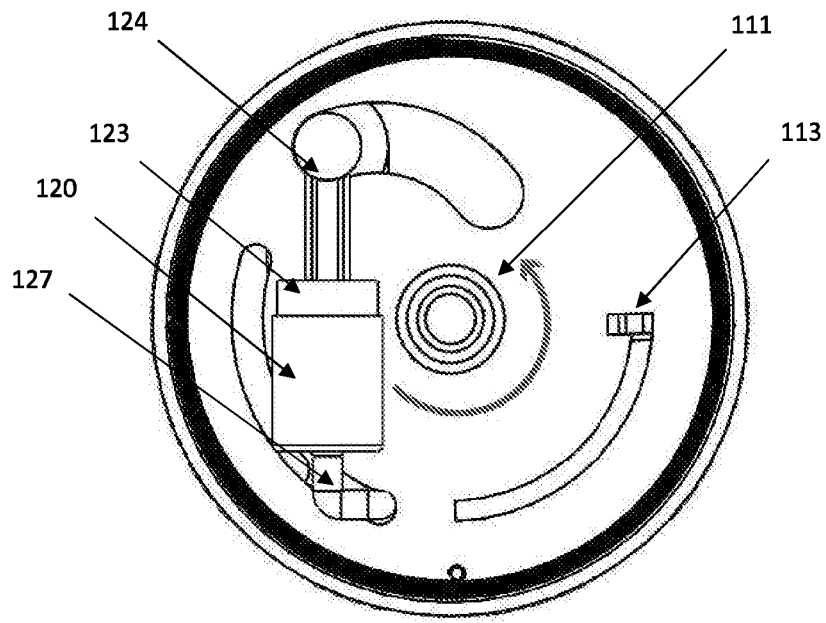
FIG. 25 is a top cut-away view of an auto-injector in a storage state before use in accordance with an embodiment of the present invention.
Figure 26:
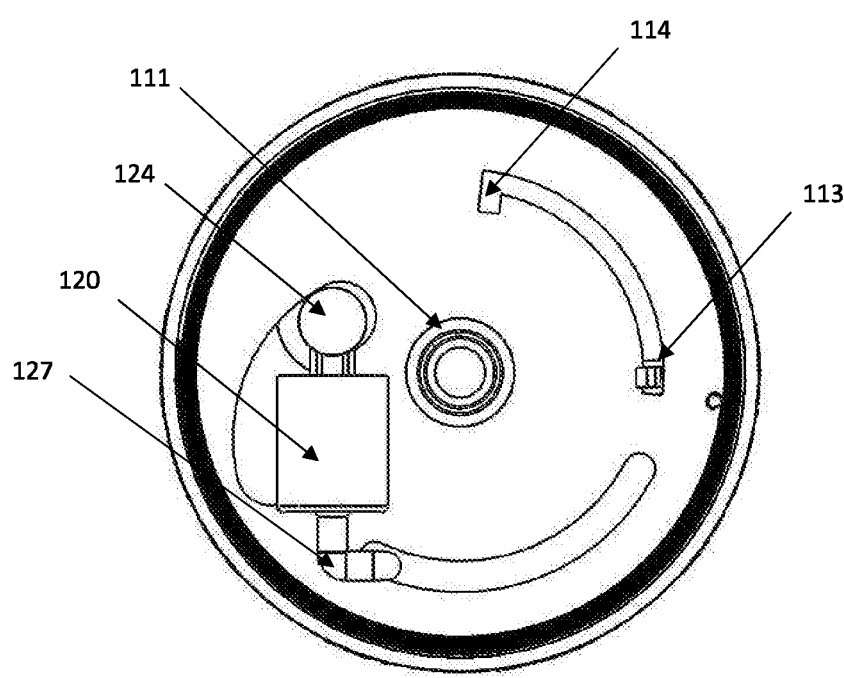
FIG. 26 is a top cut-away view of an auto-injector after use in accordance with an embodiment of the present invention.
Figure 27:
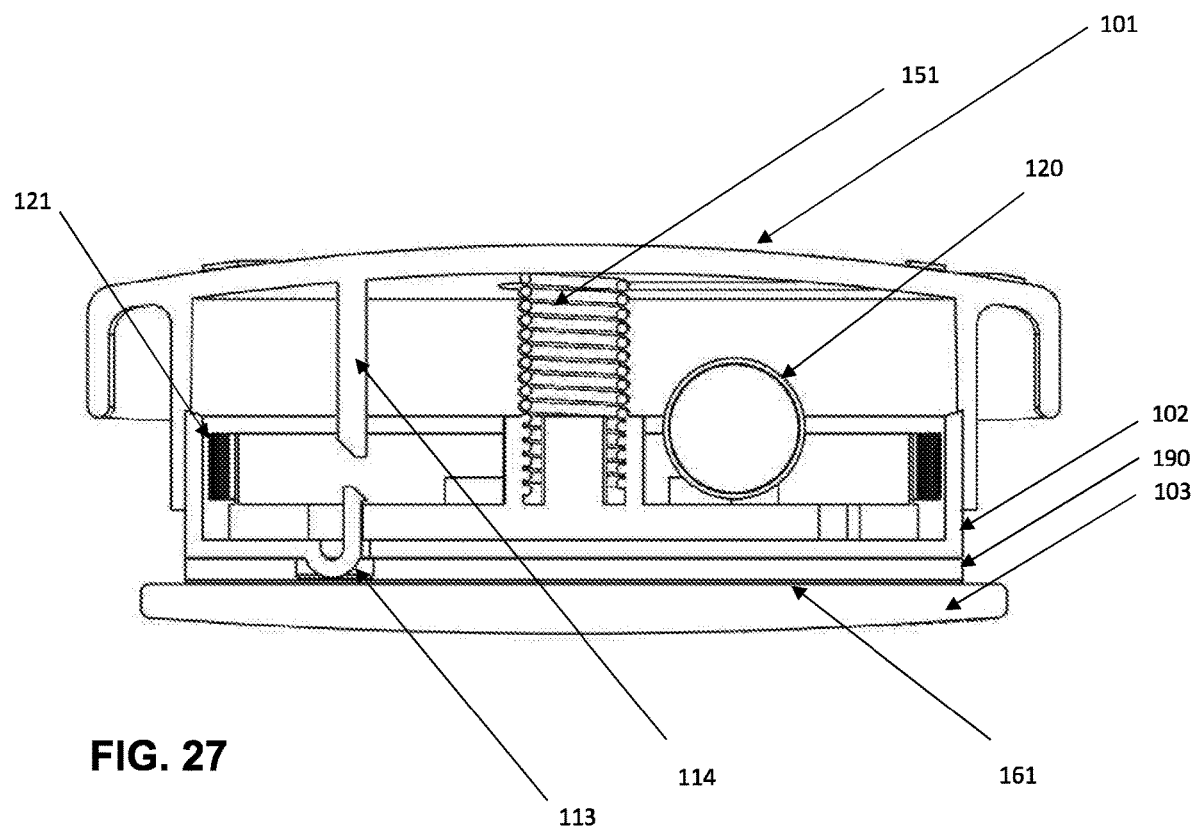
FIG. 27 is a cross-sectional view an auto-injector in a storage state before rotation preventing pin is released in accordance with an embodiment of the present invention.
Figure 28:
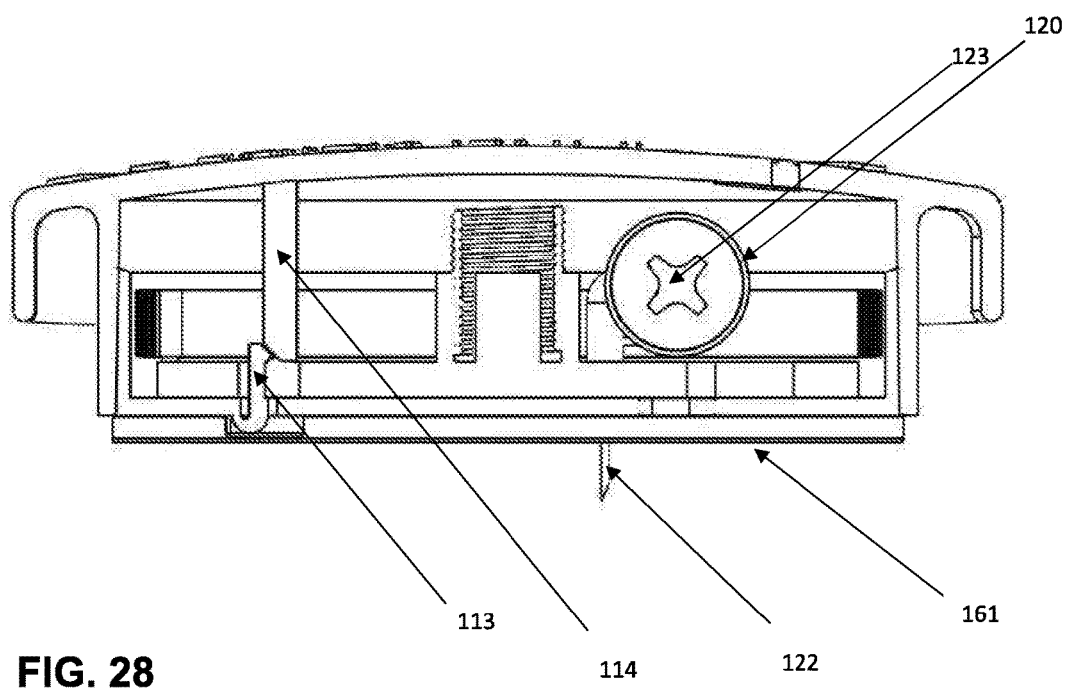
FIG. 28 is a cross-sectional view an auto-injector—after release of a rotation preventing pin in accordance with an embodiment of the current invention.
Figure 29:
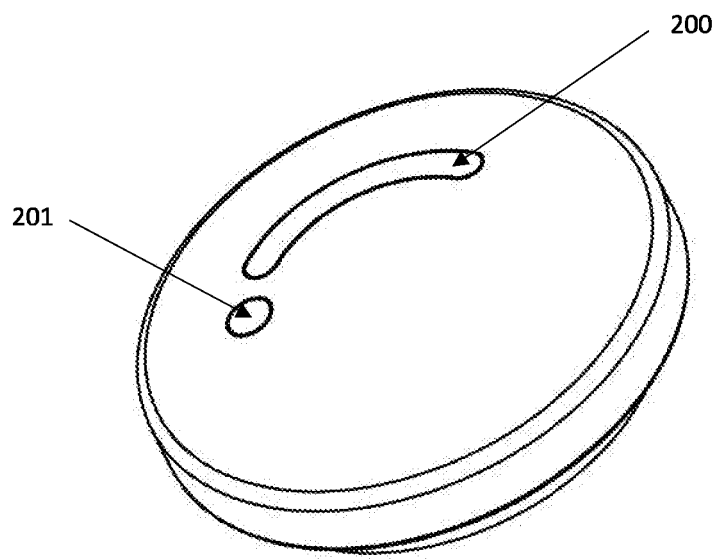
FIG. 29 is a top view of an upper housing of in accordance with an embodiment of current invention.
Figure 30:
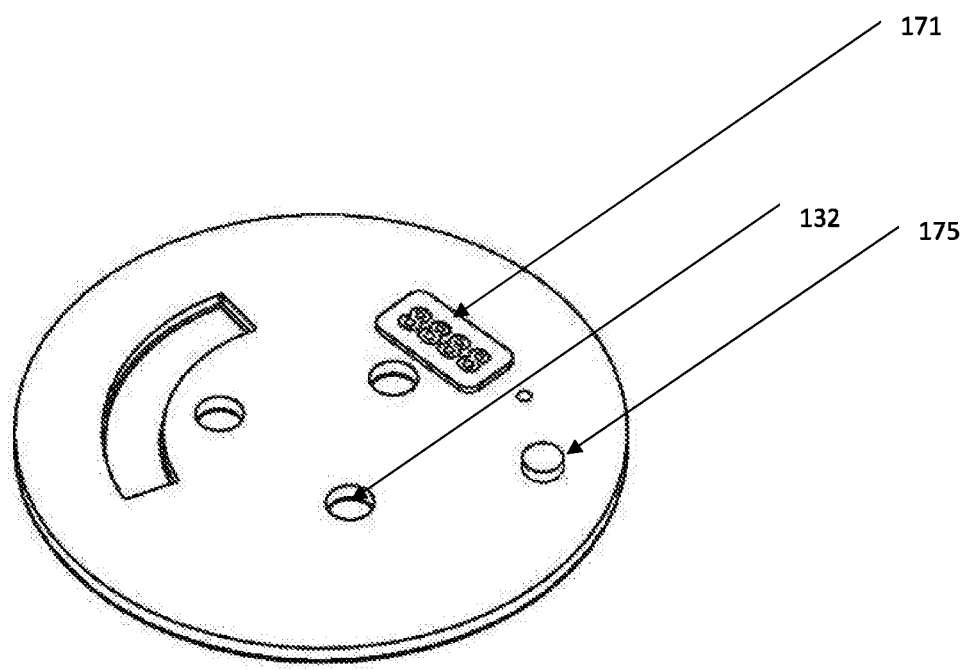
FIG. 30 illustrates a time and content indicator in accordance with an embodiment of current invention.
Figure 31:
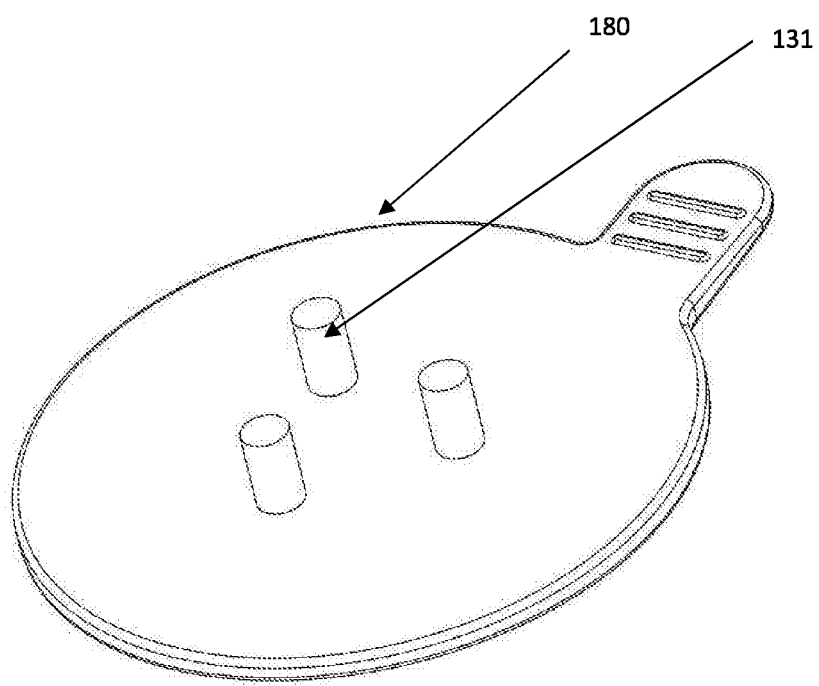
FIG. 31 detachable safety mechanism in accordance with an embodiment of current invention.
Figure 32:
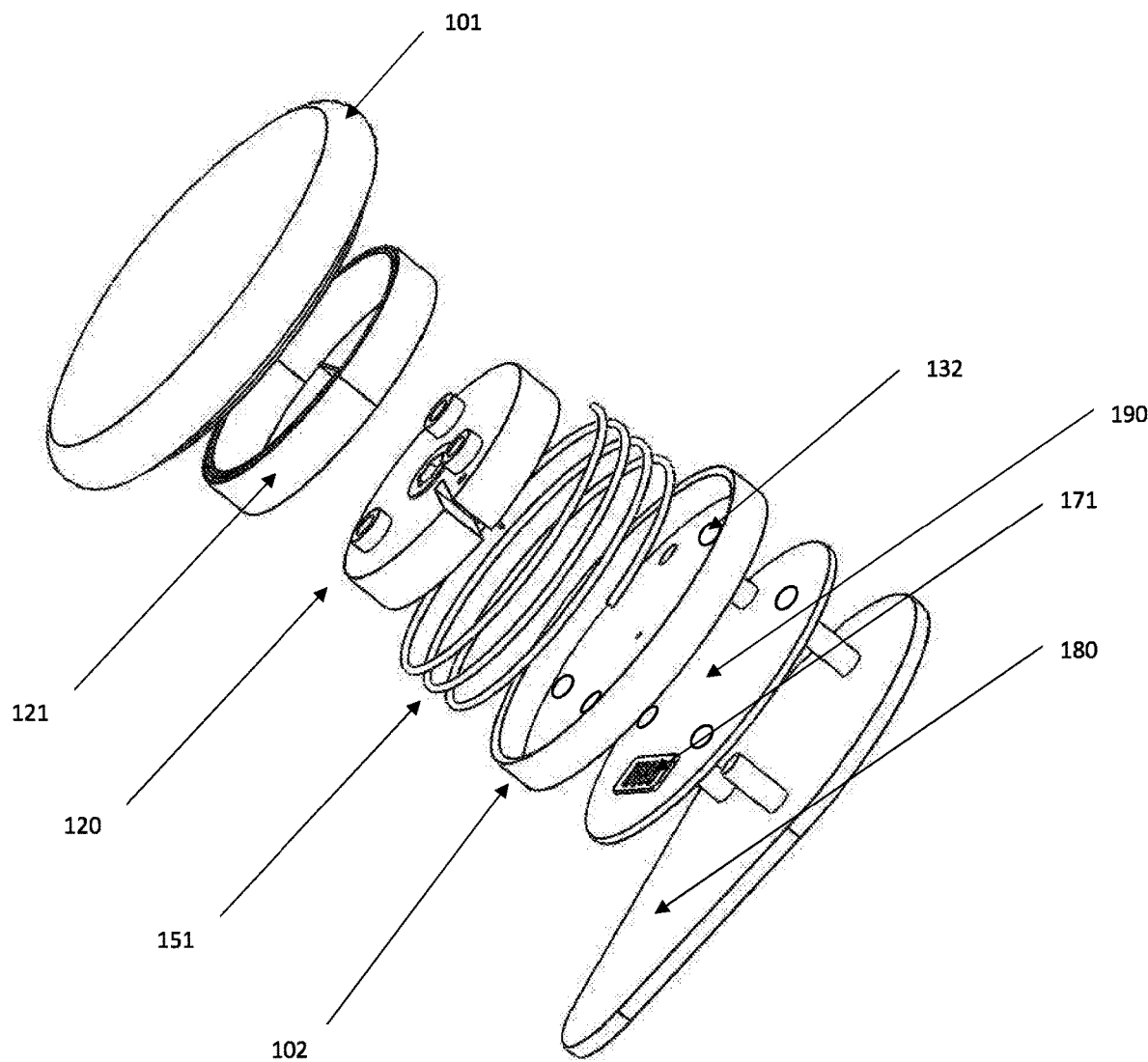
FIG. 32. is an exploded view of an auto-injector in accordance with an embodiment of the present invention.
Figure 33:
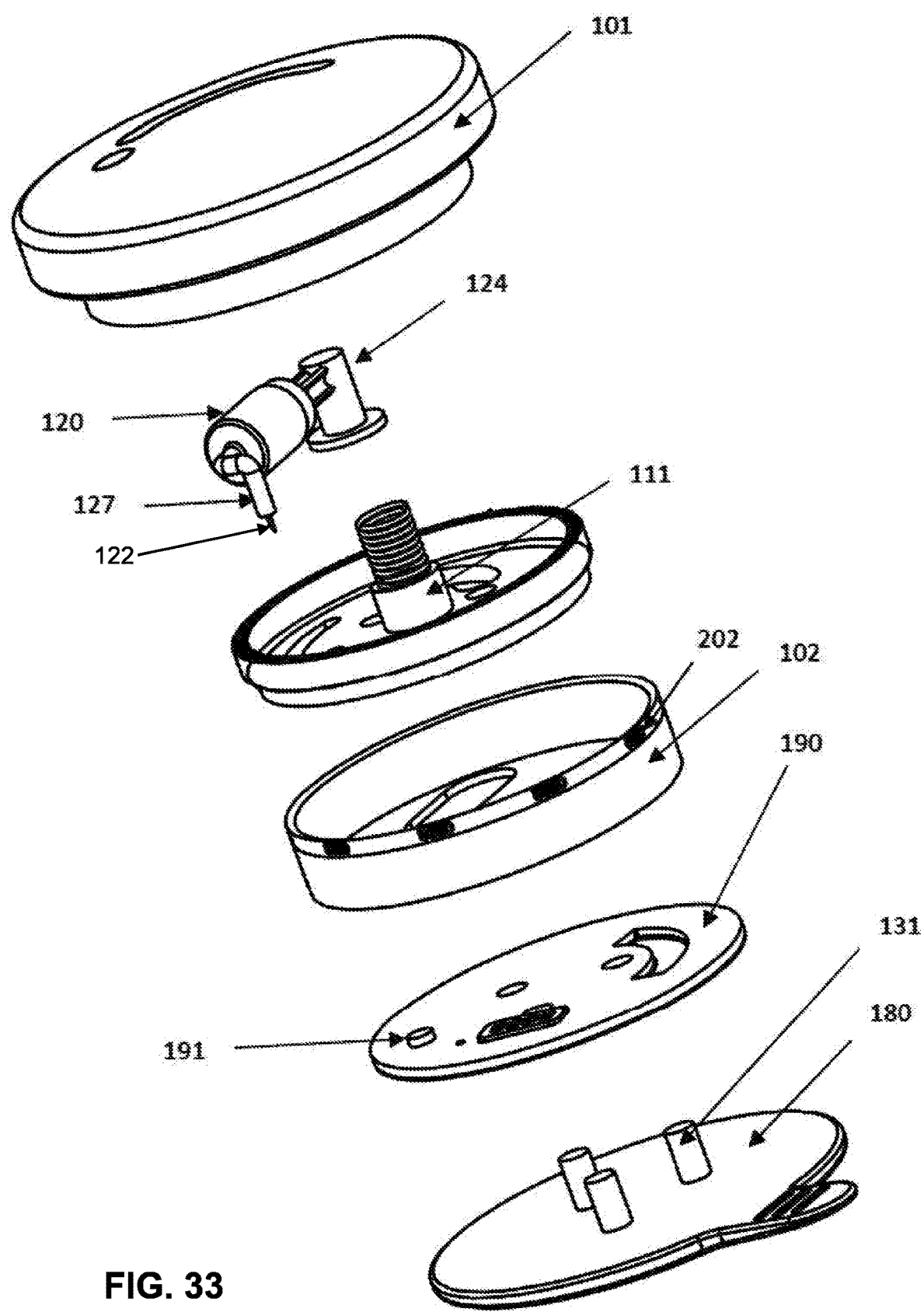
FIG. 33. is an exploded view of an auto-injector in accordance with an embodiment of the present invention.

In some embodiments, a safety mechanism 180 pulls the needle 122 out of the surface and safely stores it inside of the device after injection finishes and/or when the device is taken away from the injection site. One possible implementation of pulling the needle 122 is through the spring 151 using the stored energy from the force applied by the operator to push the upper housing 101 and the lower housing 102. In one possible implementation the injection module 150 is pushed together with the upper housing 101 away from the lower housing 102 thus pulling the needle 122 with it. The device 100 can remain attached to the patient until there is no need for it to remain there. as illustrated for example in FIG. 16. FIGS. 17, 18 and 19 illustrate movement of the drug reservoir 120 after the activation and/or the pushing of the medication out of the reservoir 120. With FIG. 10 displaying the same in one overview.

Referring to FIG. 11, auto-injection device 100 can include a predetermined aspect ratio. The aspect ratio can be a height 195 of auto-injection device 100 is a shorter length where a diameter 197 auto-injection device 100 is a longer length.

FIGS. 25-33 illustrate an injector having a cylindrical reservoir 120 in accordance with an embodiment of the current invention. Optionally, reservoir 120 is mounted with its longitudinal axis parallel (and/or at a low angle of for example between 0 to 15 degrees and/or between 15 to 30 degrees to an adhesive 161 and/or a contact surface of a lower housing 103. Optionally, rotation in a plane parallel to the axis of the reservoir 120 and/or the contact surface drives a plunger 123 into reservoir 120 and/or drive a pharmaceutical out of reservoir 120 into an injection needle 122. Optionally injection needle is mounted at a high angle with respect to the longitudinal axis of reservoir 120 (for example 90 degrees and/or between 75 to 90 degrees and/or between 45 to 75 degrees and/or between 15 to 45 degrees).

Figure 34:
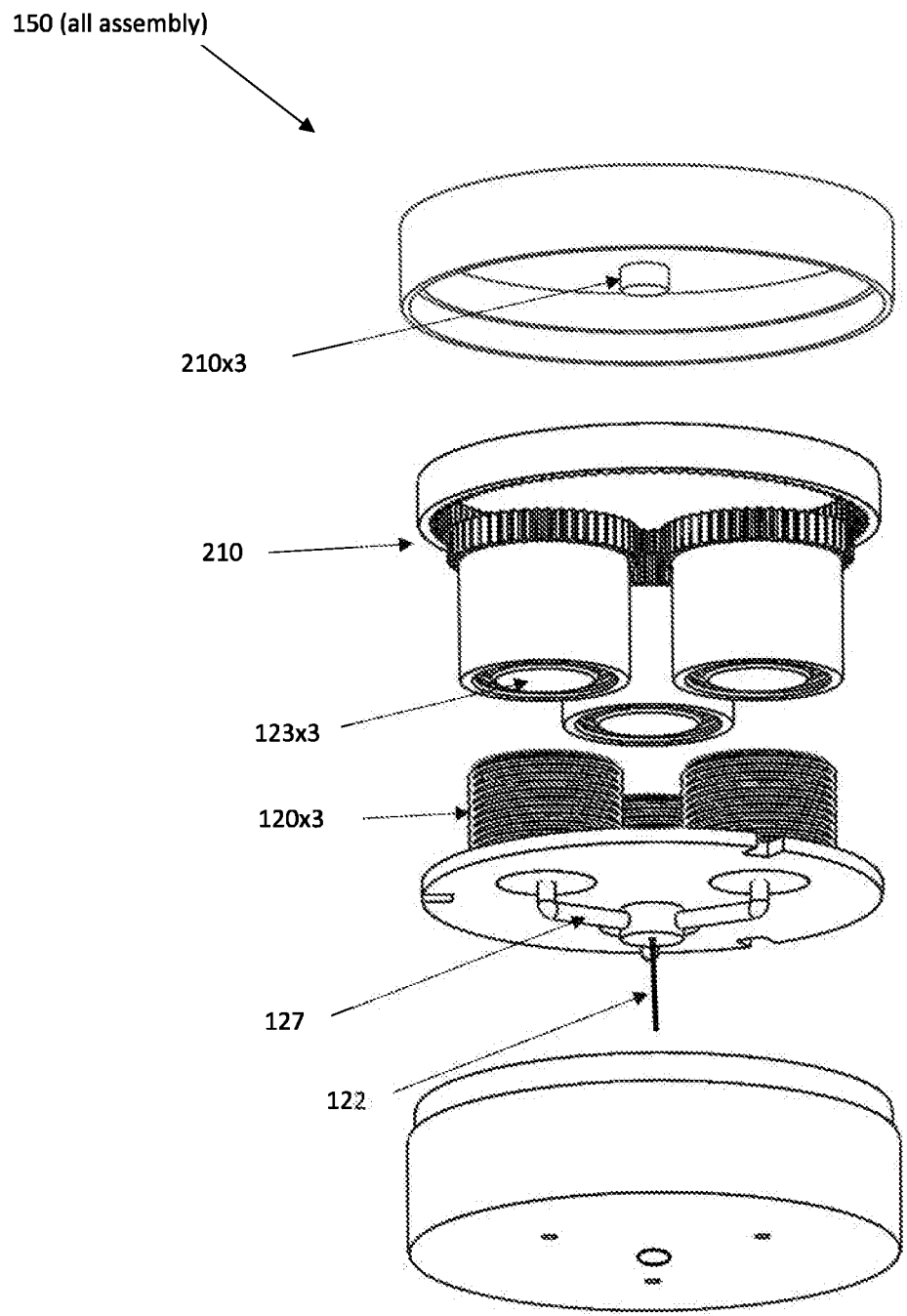
FIG. 34. is an exploded perspective view of an auto-injector in accordance with an embodiment of the present invention.
Figure 35:
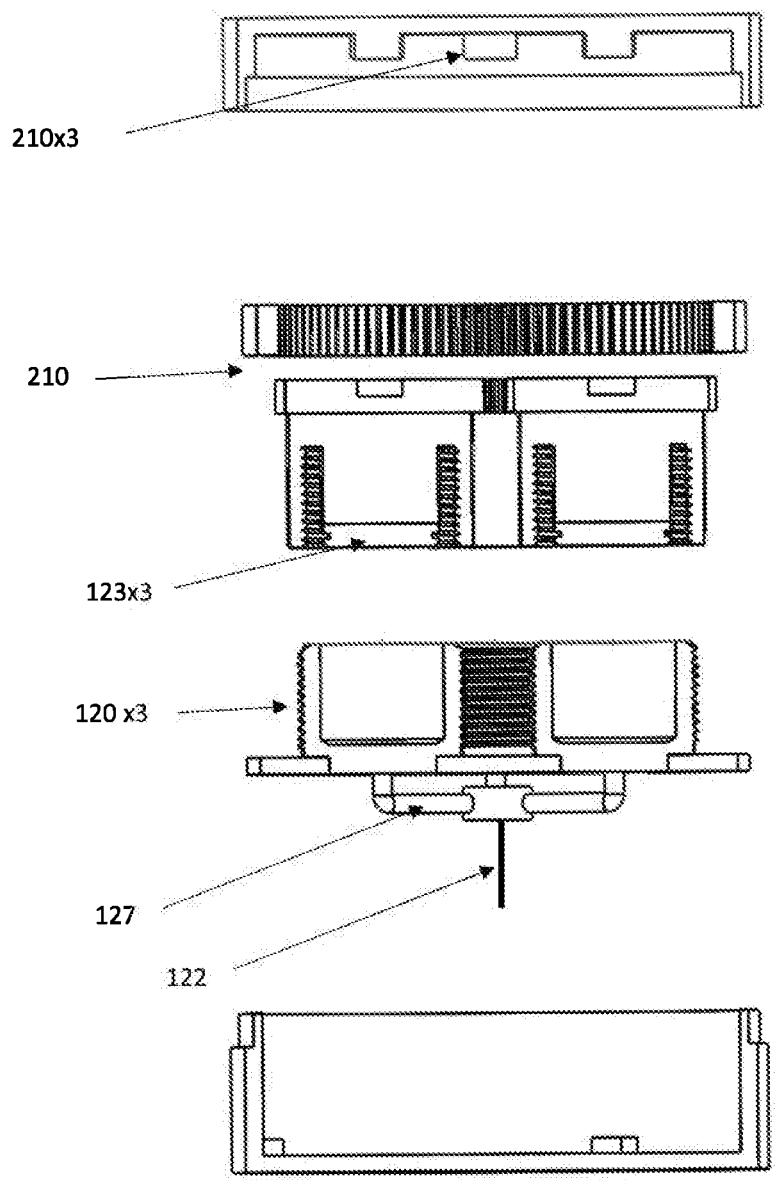
FIG. 35. is an exploded side view of an auto-injector in accordance with an embodiment of the present invention.

FIGS. 34 and 35 illustrate an injector having three cylindrical reservoirs in accordance with an embodiment of the current invention. Optionally, ring gear rotates three plunger drivers that drive three plungers 123 into three reservoirs 120. Optionally, one or more pharmaceuticals are driver out reservoirs 120 into a manifold 127 leading to an injection needle 122.

Figure 36A:
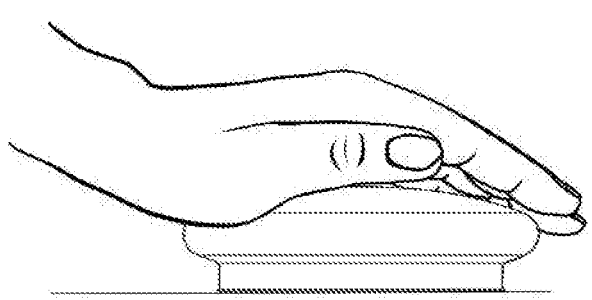
FIGS. 36A and 36B illustrate hand positions for activation and/or removal of an embodiment of the current invention in accordance with an embodiment of the current invention.
Figure 36B:
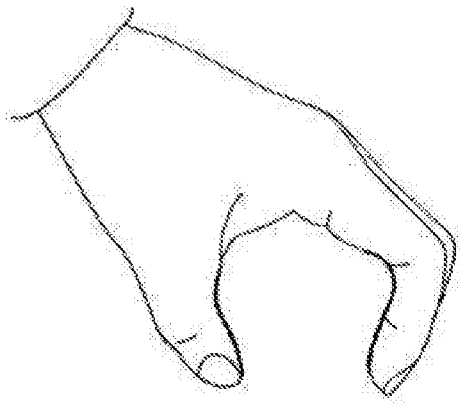

FIGS. 36A-36B show an operator's hand applying force onto auto injection device 100, according to certain embodiments.

Figure 37:
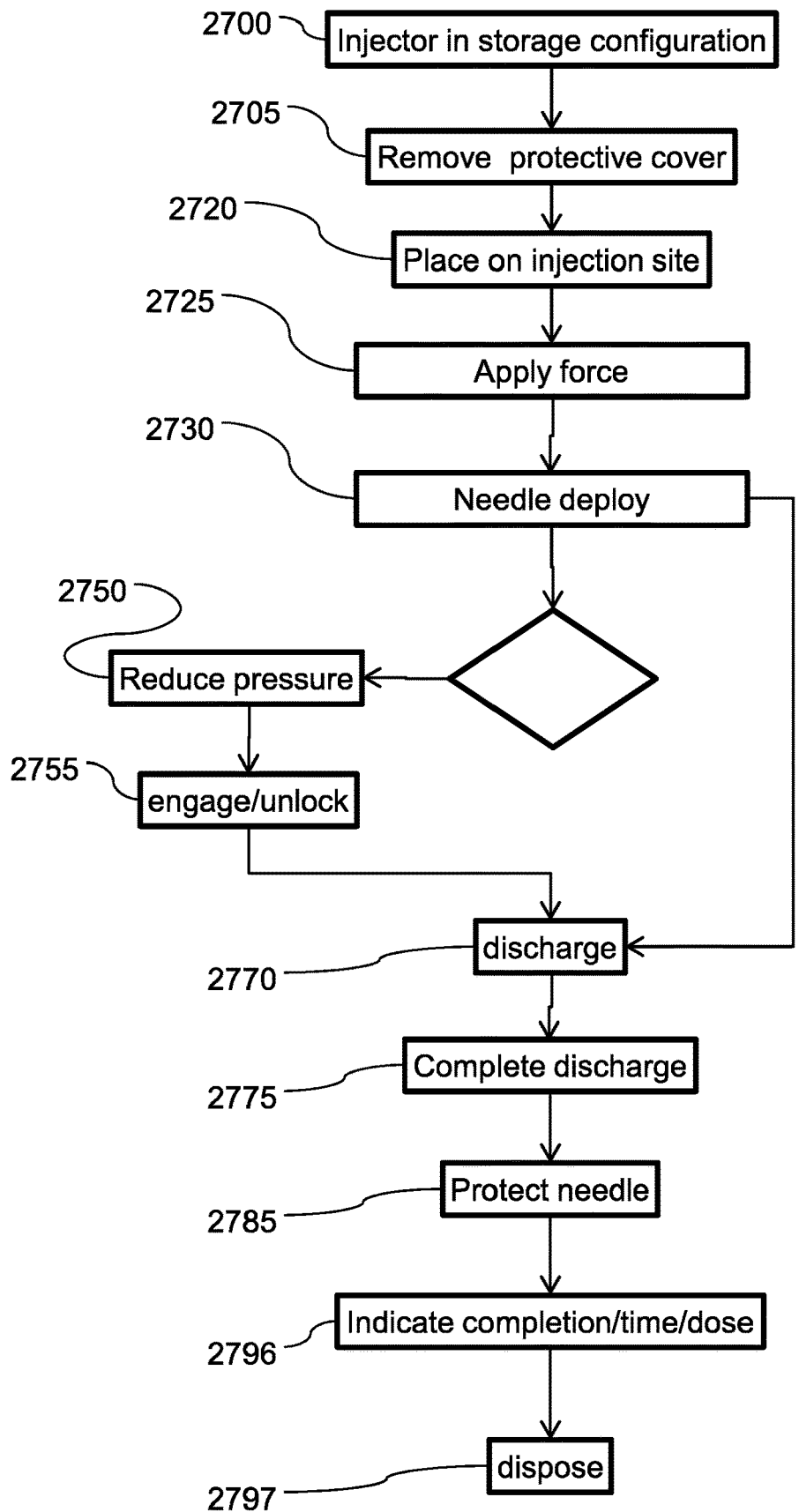
FIG. 37 is flow chart illustration of use of an autoinjector in accordance with an embodiment of the current invention.

FIG. 37 shows a method for operating auto injection device (for example device 100), according to certain embodiments. the injector is optionally supplied 2700 in a storage configuration. For example, in the storage configuration the device may have a low-profile perpendicular to a contact surface (e.g. the height perpendicular to the contact surface of the device may be less than the width thereof for example the ratio of height to width may be less than $\frac{1}{10}$ and/or less than $\frac{1}{5}$ and/or less than $\frac{1}{2}$ and/or less than 1). Optionally, in the storage configuration, a needle is shielded and/or the injector is collapsed to an easily stored state (for example with a long axis of an injection needles and/or a long dimension of a reservoir parallel and/or at an low angle (for example between 0 to 10 degrees and/or between 10 to 30 degrees and/or between 30 to 60 degrees) to a subject contact surface of the injector at the needle insertion point (e.g. a hole in the contact surface through which the needle passes upon needle extension)).

In some embodiments, the device is primed 2705 for example by removing protective cover (e.g. cover 103), for example, by pulling it away from the lower housing (e.g. housing 102). For example, the device to switch may switch to a primed state. Optionally in the primed state the device is expanded vertically with respect to the storage state and/or the injection needle is at a high angle and/or perpendicular to the contact surface. For example, in the primed state the axis of needle may be at an angle between 80 to 90 degrees and/or between 60 to 80 degrees and/or between 45 to 60 degrees to the contact surface at the needle injection point. Optionally, priming 2705 may include powering up various parts of the device. For example, a lamp may be powered up to illuminate the reservoir to allow inspection of the pharmaceutical and/or a timer may be activated.

In some embodiments, the operator may apply 2720 the auto-injection device to an injection site (e.g. an exposed surface to which medication can be injected). The auto-injection device can be applied 2720 directly to the patient's skin and/or can be applied 2720 over a garment or other material covering the patient's skin that enables injection of the medication. In some embodiments, an adhesive may attach the auto-injection device to the skin in a manner that can prevent auto-injection device from falling off the patient's skin during administration of the medication.

Step 2725 discloses the operator applying a predetermined amount of force for example to activate the device. Optionally, the force is applied perpendicular to a surface of upper housing (for example upper housing 101) resulting in the surface and/or the entire upper housing portion being pushed toward a contact surface and/or an injection site. In certain embodiments, a visual and/or a haptic and/or an oral indication can be provided to notify the operator upper housing portion has reached an activation position.

In some embodiments, upon application of the predetermined amount of force, the device may deploy 2730 to a second (e.g. deployed) state. Deployment 2730 may be autonomous (e.g. driven a stored energy in the device) and/or manual (e.g. driven by the force applied by the operator). Optionally, in the deployed state, an injection needle (for example needle 122) may extend out the injector and/or can penetrate the skin and/or reach a predetermined injection depth. The length of extension of the needle may take into consideration a width of a garment on the subject's skin.

In some embodiments, reduction 2750 of the application of pressure onto auto-injection device can result in engaging 2755 and/or unlocking a discharge mechanism. For example, unlocking may include an elevating spring (e.g. spring 151) pushing upper housing portion away from a drug reservoir (e.g. drug reservoir 120). Optionally in the engaged state the device may be ready to discharge a payload. For example, engaging 2755 may cause rotation preventing pins 112 to exit rotation preventing sockets 124, and rotational spring 121 can apply a force onto to injection reservoir, which can start rotating, thus activating and administering the medication into the patient.

In certain embodiments, engaging and/or unlocking occur directly as a result of applying 2725 force to deploy 2730 the needle. For example, the preventing pins 112 can break due to the force applied 2725 by the operator on the upper part so that the injection module is activated already after the needle penetrates the surface and the operator can continue applying pressure to the auto injection device. In certain embodiments, the injection may commence during the time that pressure is applied 2725 to the auto-injection device.

In some embodiments a pharmaceutical is discharged 2770 to the subject.

After a full dosage of the pharmaceutical has been injected and/or after the entire contents of a reservoir is injected an activation display mechanism can display a notification that the injection is complete 2796. Alternatively or additionally a mechanism may display a time of injection (e.g. either when the device was primed and/or deployed and/or activated and/or when injection began and/or when injection ended) and/or a dosage (for example a full dose and/or a not a full dose and/or partial dose for example if discharge ended prematurely). In certain embodiments, an additional time display mechanism 171 can be triggered to display a time and date of injection. Alternatively or additionally, a safety mechanism 180 can be triggered to protect 2785 the needle and/or remove an injection needle. For example, the safety mechanism may pull the needle out of the surface and safely store it inside of the auto-injection device. In certain embodiments, the needle may be pulled by a spring. The spring may use energy stored from when the device was in the storage configuration and/or new stored energy from the force applied by the operator to push the upper housing portion and/or the bottom housing portion. In certain embodiments, the reservoir is pulled together with the needle and/or the upper housing portion away from the bottom housing portion to retract the injection needle. Optionally a locking mechanism may lock the needle in a retracted position and/or hold the injector in the expanded position for example to prevent re-exposure of the needle. Alternatively or additionally, the needle may be translated and/or rotated in such a way that it is no longer aligned with a needle opening. Alternatively or additionally, the needle hole may be translated and/or blocked to prevent re-exposure of the needle.

Figure 16:
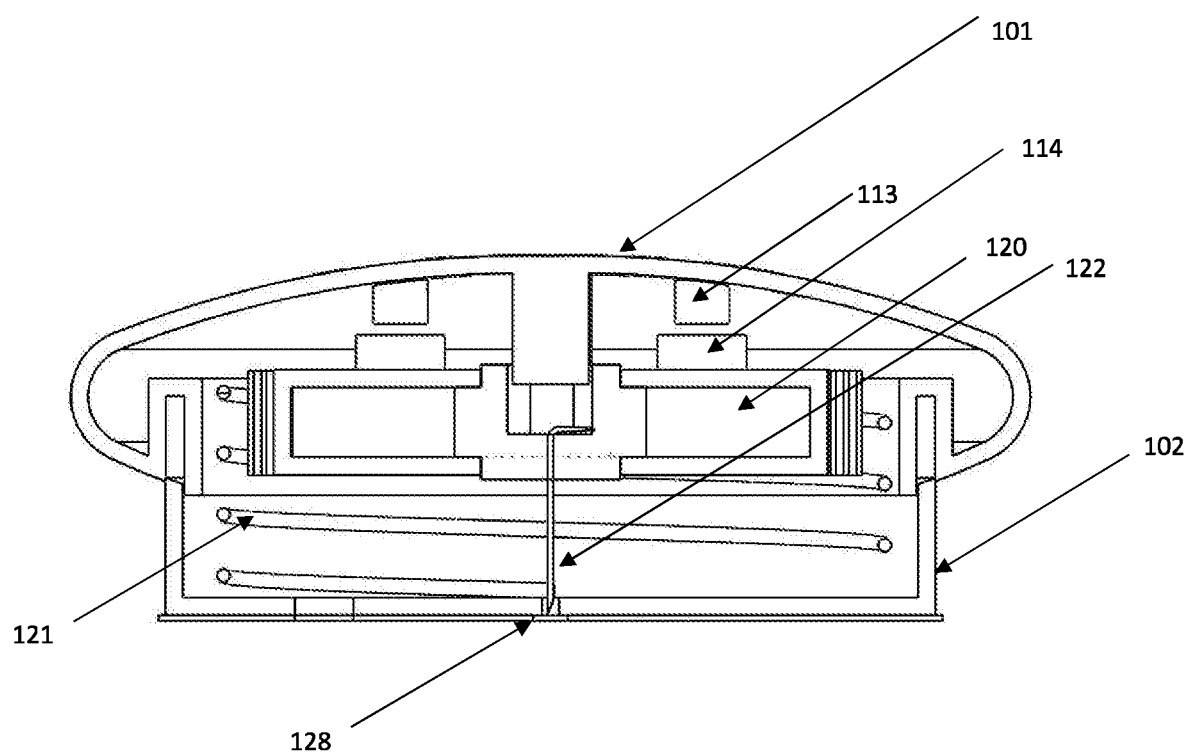
FIG. 16 is a cross-sectional side view of an autoinjector after discharge of a drug in accordance with an embodiment of the present invention.

The auto-injection device can remain attached to the patient until there is no need for it to remain there as illustrated in FIG. 16. FIGS. 7, 8 and 9 show movement of the drug reservoir after activation and pushing of the medication out of the drug reservoir.

FIGS. 36A and 36B illustrate hand positions for activation and/or removal of an embodiment of the current invention in accordance with an embodiment of the current invention. Optionally the injector may be activated by pushing a large surface encouraging a user for example to push the activation surface without grasping the injector, for example with a flat hand, for example as illustrated in FIG. 36A. Optionally to pull the injector away from the injection site one would move his hand from the activation position to grasp the walls of the device (for example as illustrated in FIG. 36B). Moving the hand from the position of pushing to the position of pulling may require time inhibiting pulling away of the injector from the injection before discharge of the pharmaceutical has finished.

Referring to FIG. 37 showing a method for use of the auto-injection device, according to certain embodiments. The auto injection device is optionally supplied 2700 in an initial state (e.g. a storage configuration) position.

In some embodiments, the device is primed 2705, for example by removing a protective cover is removed.

Optionally an operator holds the auto-injection device and/or moves the device towards a patient's body.

Optionally the device is placed 2720 onto an injection site. For example, the device may be primed 2705 and then place 2720 on the injection site. Alternatively or additionally, the device may be placed 2720 on the injection site and then primed 2705. Optionally, placing 2720 the device onto an injection site may include adhering auto-injection device to a subject, e.g. a patient.

In some embodiments, a force may be applied 2725 to auto-injection device. For example, the force may to overcome a mechanical threshold.

In some embodiments, a needle may be deployed 2730. For example, overcoming the mechanical threshold may move the device into a second position wherein the needle is deployed 2730.

Optionally a rotation prevention mechanism may be engaged. In some embodiments, reducing 2750 pressure on the auto-injection device may unlock 2755 a discharge mechanism (for example by releasing a rotation prevention mechanism).

In some embodiments a pharmaceutical (e.g. a medication) may be discharged 2770. For example, discharge may be through an injection needle into a subject. For example, discharging may be driven by rotating injection module. Optionally discharge may be completed 2775. For example, discharge may be completed 2775 when the injection module completes its rotation, Optionally the device may enter a fourth position and/or provide an indication 2796 that injection is complete. Alternatively or additionally, the device may indicate 2796 a time and/or dosage of injection and/or a failure warning. Optionally, the indicator may be part of the device and/or the device may remain attached to the subject. Alternatively or additionally, the indicator may be separated from the device and connected to the subject.

In some embodiments, an injection needle is protected 2785. For example, protection 2785 a needle may include retracting the needle into auto-injection device. Alternatively or additionally, a needle sleeve may be positioned over the needle. Protection 2785 may occur on completing 2775 of discharge and/or on an error condition (for example when the device is removed prematurely).

Optionally, the device may be disposed of 2797. For example, disposal 2797 may be after the drug has been administered for example by the operator. Alternatively or additionally, the operator may leave the device with the subject for reference by medical personnel subsequently treating the subject. The subsequent medical personnel may discard the device.

Figure 38:
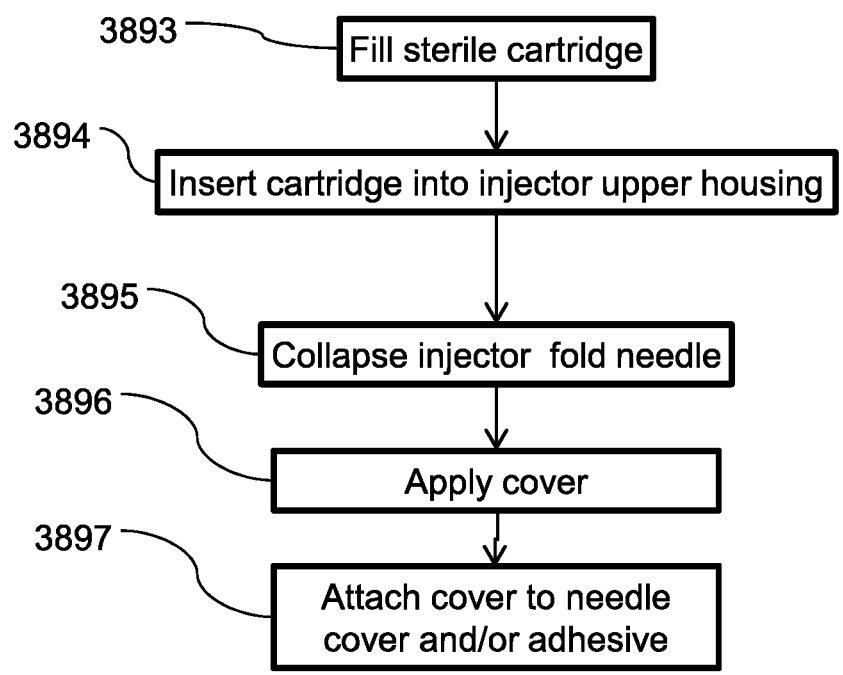
FIG. 38 is a flow chart illustration of a method of assembly of an injector in accordance with an embodiment of the current invention.

FIG. 38 is a flow chart illustration of a method of assembly of an injector in accordance with an embodiment of the current invention.

It is expected that during the life of a patent maturing from this application many relevant technologies will be developed and the scope of the terms in the present disclosure is intended to include all such new technologies a priori.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

FIG. 38 is a flow chart illustration of a method of assembling a pharmaceutical delivery device in accordance with an embodiment of the current injection. In some embodiment, a cartridge is filled 3893 in a sterile and/or aseptic environment. For example, the cartridge may include a cylindrical reservoir and/or be configured for filling 3893 with standard and/or minimally modified filling equipment. Optionally, the sterility of the cartridge may be protected from the time of filling 3893, for example with a needle cap and/or a plunger. Optionally a needle may be integrally connected to the reservoir during filling and/or in the aseptic filling device. Optionally, the needle may be rigidly connected to the reservoir during filling and/or in the aseptic filling device.

In some embodiments, the cartridge may be inserted 3894 into the injector with its sterility intact from filling. For example, the cartridge may be inserted 3894 into the injector with the needle cap in place.

In some embodiments, an injector may be collapsed 3895 into a storage configuration. For example, the needle may be collapsed and/or folded and/or rotated to be at a low angle to a contact surface. For example, while the injector is being collapsed 3895 and/or telescoped and/or pushed together to a storage configuration the needle and/or reservoir of the cartridge may be rotated. For example, the cartridge may be rotated around a longitudinal axis of a cylindrical reservoir. For example, a wall of a contact surface may push the needle into the storage position while the device in collapsed 3895.

In some embodiment, a cover is placed 3896 onto the injector. Optionally the cover is place after collapsing 3895. Optionally, the cover holds the injector in the storage configuration and/or protects the internal parts of the injector and/or a contact surface and/or an adhesive for contamination. For example, the cover may protect from water and/or dust.

In some embodiments, the device cover is attached 3897 to the needle sleeve. For example, attaching 3897 may be in such a way that pulling the cover off the device cover also pulls off the needle sleeve.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An intramuscular auto-injector comprising:
   a contact surface contoured to fit a body surface;
   a storage state having a low-profile perpendicular to said contact surface wherein a height of the injector perpendicular to said contact surface in the storage state is less than ½ a width of said contact surface;
   a cover protecting said contact surface; and
   a priming mechanism coupled to said cover wherein removal of said cover activates said priming mechanism, for priming the injector from said storage state to a primed configuration, and wherein a height of the injector in the primed state measured perpendicular to the contact surface is greater than the height of the injector in the storage state measured perpendicular to the contact surface.

2. The injector of claim 1, further comprising an injection needle and wherein in said storage state an axis of said injection needle is oriented at an angle of less than 45 degrees with said contact surface and said priming mechanism is coupled to said injection needle for rotating said injection needle to an angle of greater than 45 degrees with said contact surface in said primed configuration.

3. The injector of claim 2, wherein said injection needle is rigidly attached to a drug reservoir and wherein said rotating includes rotating said drug reservoir.

4. The injector of claim 3, wherein said rotating is around an axis of said drug reservoir.

5. The injector of claim 3, wherein said injector is configured to treat an emergency life threatening condition.

6. The injector of claim 5, wherein said emergency life threatening condition includes at least one of a chemical attack, an animal bite deadly poison and an allergic reaction.

7. The injector claim 2, wherein said height of the injector in the storage state is less than twice a length of said injection needle.

8. The injector of claim 1, wherein said injector has cylindrical shape and said contact surface forms an end of said cylindrical shape.

9. The injector claim 8, wherein the injector telescopes between said storage state and said primed configuration.

10. The injector of claim 1, further comprising an elastic energy storage device
    connected to said priming mechanism and wherein stored energy in said elastic energy storage device drives an increasing of said height of the injector between the storage state and the primed configuration.

11. The injector of claim 10, further comprising an elastic forcing member connected to
    an injection needle and wherein said elastic forcing member applies a force pushing a tip of said injection needle towards said contact surface in said primed configuration.

12. The injector of claim 1, wherein the injector includes a cavity in which a drug is stored and wherein in said stored state said cover is seals around said contact surface to prevent moisture from outside the injector from reaching said cavity.

13. The injector of claim 12, further comprising an injection needle and a needle sleeve sealing said injection needle from said cavity.

14. The injector of claim 13, wherein said needle sleeve is attached to said cover.

15. A method of intermuscular injection of a drug comprising:
    providing an injector having a distal end, the injector in a storage state having low profile perpendicular to a contact surface on the distal end of the injector and a cover covering said contact surface,
    and wherein a height of said injector measured perpendicular to the contact surface in said storage state is less than a half of a width of said contact surface;
    removing the cover from the contact surface;
    priming said injection in response to said removing and wherein said priming includes increasing said height;
    placing said contact surface on a surface of a subject;
    pushing a proximal end of the injector towards said contact surface; and
    extending a point of an injection needle out a hole in said contact surface into said subject in response to said pushing.

16. The method of claim 15, further comprising:
    rotating the injection needle from an angle of less than 45 degrees to said contact surface in said storage state to an angle of greater than 45 degrees to said contact surface in a primed state.

17. The method of claim 16, wherein said injection needle is rigidly attached to a drug reservoir, wherein said rotating further comprises rotating said drug reservoir.

18. The method of claim 17, wherein said rotating is around an axis of said drug reservoir.

19. The method of claim 15, wherein said injector has a cylindrical shape, and wherein said contact surface forms and end of said injector and wherein said increasing said height include telescopic lengthening of said injector.

* * * * *